(12) United States Patent
Mercep et al.

(10) Patent No.: US 7,579,334 B2
(45) Date of Patent: Aug. 25, 2009

(54) COMPOUNDS WITH ANTI-INFLAMMATORY ACTIVITY

(75) Inventors: Mladen Mercep, Zagreb (HR); Milan Mesic, Zagreb (HR); Linda Tomaskovic, Zagreb (HR)

(73) Assignee: GlaxoSmithKline Istrazivacki Centar Zagreb, Zagreb (HR)

( * ) Notice: Subject to any disclaimer, the term of this patent is extended or adjusted under 35 U.S.C. 154(b) by 781 days.

(21) Appl. No.: 10/830,858

(22) Filed: Apr. 22, 2004

(65) Prior Publication Data

US 2005/0080003 A1    Apr. 14, 2005

(30) Foreign Application Priority Data

Apr. 24, 2003   (HR)   ............... P 20030324 A

(51) Int. Cl.
*A61K 31/585*   (2006.01)
*A61K 31/395*   (2006.01)
*C07J 17/00*    (2006.01)

(52) U.S. Cl. .................. 514/175; 514/183; 540/114; 540/467

(58) Field of Classification Search ............... 540/114, 540/467; 514/175, 183
See application file for complete search history.

(56) References Cited

U.S. PATENT DOCUMENTS

| 6,297,260 | B1 | 10/2001 | Bandarage et al. |
| 7,091,187 | B2 | 8/2006 | Mercep et al. |
| 7,109,176 | B2 | 9/2006 | Mercep et al. |
| 7,157,433 | B2 | 1/2007 | Mercep et al. |
| 2004/0005641 | A1 | 1/2004 | Burnet et al. |
| 2004/0087517 | A1 | 5/2004 | Burnet et al. |
| 2004/0186063 | A1 | 9/2004 | Gutke et al. |
| 2005/0171342 | A1 | 8/2005 | Burnet et al. |

FOREIGN PATENT DOCUMENTS

| EP | 0283055 A2 | 9/1988 |
| EP | 0283055 B1 | 9/1988 |
| EP | 0771564 | 5/1997 |
| EP | 0775489 | 5/1997 |
| WO | 9213872 | 8/1992 |
| WO | 9213873 | 8/1992 |
| WO | 94/13690 A1 | 6/1994 |
| WO | 9414834 | 7/1994 |
| WO | 0042055 | 7/2000 |
| WO | 0187890 | 11/2001 |
| WO | 02055531 | 7/2002 |
| WO | WO-02/055531 A1 | 7/2002 |
| WO | 03/070174 A2 | 8/2003 |
| WO | 2004/005309 A2 | 1/2004 |
| WO | 2004/005310 A2 | 1/2004 |
| WO | 2004/005313 A2 | 1/2004 |

OTHER PUBLICATIONS

Vippagunta et al. (Advanced Drug Delivery Reviews, 48 (2001), pp. 3-26) state "Predicting the formation of solvates or hydrates of a compound and the number of molecules of water or solvent incorporated in to the crystal lattice of a compound is complex and difficult." See p. 18, section 3.4.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta et al. (Advanced Drug Delivery Reviews, 48 (2001), pp. 3-26).*

(Continued)

*Primary Examiner*—Barbara P Badio
(74) *Attorney, Agent, or Firm*—J. Michael Strickland

(57) ABSTRACT

The present invention relates to new compounds represented by Formula I:

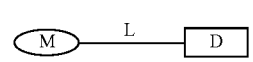

wherein M represents a macrolide subunit of the substructure II:

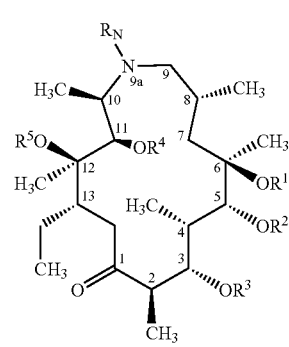

L represents the chain of the substructure III:

$$-X^1-(CH_2)_m-Q-(CH_2)_n-X^2-$$    III

D represents the steroid or nonsteroidal subunit derived from steroid or nonsteroidal (NSAID) drugs with anti-inflammatory activity;

The present invention relates also to pharmaceutically acceptable salts and solvates of such prepared compounds, to process and intermediates for their preparation, as well as to the improved therapeutic action and the use in the treatment of inflammatory diseases and conditions in humans and animals.

48 Claims, No Drawings

OTHER PUBLICATIONS

Costa and Vilarrasa, "Hybrids of macrolides and nucleobases or nucleosides." Tetrahedron Letters, 41:3371-3375 (2000).

Gladue, R. P., et al.; In Vitro and In Vivo Uptake of Azithromycin (*CP-62,993) by Phagocytic Cells: Possible Mechanism of Delivery and Release at Sites of Infection; Antimicrob. Agents Chemother.; 1989; 3; 277-282.

Abdelghaffar et al.; "Erythromycin A-Derived Macrolides Modify the Functional Activities of Human Neutrophils by Altering the Phospholipase D-Phosphatidate Phosphohydrolase Transduction Pathway: L-Cladinose Is Involved Both in Alterations of Neutrophil Functions and Modulation of This Transductional Pathway"; Journal of Immunology; 1997; vol. 159, No. 8; pp. 3995-4005.

Labro; "Anti-Inflammatory Activity of Macrolides: A New Therapeutic Potential?"; Journal of Antimicrobial Chemotherapy; 1998; vol. 41, Suppl. B; pp. 37-46.

Mikasa et al.; "The Anti-Inflammatory Effect of Erythromycin in Zymosan-Induced Peritonitis of Mice"; Journal of Antimicrobial Chemotherapy; 1992; vol. 30; pp. 339-348.

U.S. Appl. No. 10/250,934, filed Dec. 29, 2003.
U.S. Appl. No. 11/201,685, filed Aug. 10, 2005.
U.S. Appl. No. 11/355,808, filed Feb. 15, 2006.
U.S. Appl. No. 11/813,882, filed Jul. 13, 2007.
U.S. Appl. No. 11/813,884, filed Jul. 13, 2007.
U.S. Appl. No. 11/718,505, filed May 2, 2007.

* cited by examiner

SEQUENCE LISTING

<160> NUMBER OF SEQ ID NOS: 2

<210> SEQ ID NO 1
<211> LENGTH: 39
<212> TYPE: DNA
<213> ORGANISM: artificial sequence
<220> FEATURE:
<223> OTHER INFORMATION: primer

<400> SEQUENCE: 1
atatggatcc ctgatggact ccaaagaatc attaactcc         39

<210> SEQ ID NO 2
<211> LENGTH: 36
<212> TYPE: DNA
<213> ORGANISM: artificial sequence
<220> FEATURE:
<223> OTHER INFORMATION: primer

<400> SEQUENCE: 2
atatctcgag ggcagtcact tttgatgaaa cagaag            36

COMPOUNDS WITH ANTI-INFLAMMATORY ACTIVITY

PRIORITY CLAIM

This Application claims priority to Croatian patent application HR P20030324 filed Apr. 24, 2003 herein incorporated by reference in its entirety.

SUMMARY OF THE INVENTION

The present invention relates to: a) new compounds represented by the structure I:

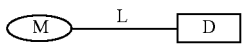

I wherein M represents a macrolide subunit derived from macrolides, possessing the property of accumulation in inflammatory cells, D represents either a steroid subunit or nonsteroidal subunit derived from nonsteroidal anti-inflammatory drugs (NSAID), and L represents a chain linking M and D; b) their pharmacologically acceptable salts and solvates; c) processes and intermediates for their preparation and d) their activity and use in the treatment of inflammatory diseases and conditions in humans and animals.

Specifically the macrolide subunit is an azithromycin aglycone subunit and the linkage to D is effected via the linker L through the nitrogen at position 9a of the aglycone subunit.

BACKGROUND OF THE INVENTION

Anti-inflammatory medicaments can be classified into those of steroid and of nonsteroidal type. Steroid anti-inflammatory compounds are still the most effective ones in the treatment of inflammatory diseases and conditions such as: asthma, chronic obstructive pulmonary disease, inflammatory nasal diseases such as allergic rhinitis, nasal polyps, intestinal diseases such as Crohn's disease, colitis, ulcerative colitis, dermatological inflammations such as eczema, psoriasis, allergic dermatitis, neurodermatitis, pruritis, conjunctivitis and rheumatoid arthritis. In addition to excellent potency and effectiveness, medicaments of this type also possess numerous unfavourable side-effects, (e.g. disturbance of carbohydrate metabolism, decreased calcium resorption, decreased excretion of endogenous corticosteroids and disturbance of physiological functions of the pituitary gland, adrenal cortex and thymus. Steroids present on the market are highly effective against inflammatory conditions and processes whereas their systemic side-effects are diminished. Patent applications WO 94/13690; 94/14834; 92/13872 and 92/13873 describe the so-called "soft" steroids or hydrolysable corticosteroids designed for topical application at the inflammation site, whereas their systemic side-effects are diminished due to the hydrolysis in the serum, wherein the active steroid very rapidly hydrolyses into the inactive form. An ideal steroid, however, without unfavourable effects in a long-term and continuous treatment as required for the control of diseases such as asthma or Crohn's disease has yet to be found, so that there are intense efforts on the discovery and development of steroids with improved therapeutic profile.

Macrolide antibiotics accumulate preferentially within different cells of subjects, especially within phagocyte cells such as mononuclear peripheral blood cells, and peritoneal and alveolar macrophages. (Gladue, R. P. et al, Antimicrob. Agents Chemother. 1989, 33, 277-282; Olsen, K. M. et al, Antimicrob. Agents Chemother. 1996, 40, 2582-2585). Inflammatory effects of some macrolides have been described in the literature, although their effects are relatively weak. For example, the anti-inflammatory effect of erythromycin derivatives (J. Antimicrob. Chemother. 1998, 41, 37-46; WO Patent Application No. 00/42055) and azithromycin derivatives has been described (EP Pat. Br. 0283055). Anti-inflammatory effects of some macrolides are also known from in vitro and in vivo studies in experimental animal models such as in zymosan-induced peritonitis in mice (J. Antimicrob. Chemother. 1992, 30, 339-348) and endotoxin-induced neutrophil accumulation in rat trachea (J. Immunol. 1997, 159, 3395-4005). The modulating effect of macrolides upon cytokines such as interleukin 8 (IL-8) (Am. J. Respir. Crit. Care. Med. 1997, 156, 266-271) and interleukin 5 (IL-5) (EP Pat. Br. 0775489 and EP Pat. Br. 771564) is known as well.

HR Patent Application No. 20010018, WO 04/005309, WO 04/005310 and WO 02/005531 herein incorporated by reference in their entireties describe compounds of the form:

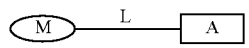

wherein M represents a macrolide subunit possessing the property of accumulation in inflammatory cells, A represents an anti-inflammatory subunit which can be steroid or nonsteroidal and L represents a chain linking M and A, and improved therapeutic action of these compounds in the treatment of inflammatory diseases and conditions The macrolide portion of the conjugate has always one or two sugar moities Compounds in which the steroid or nonsteroidal subunit are linked to the macrolide subunit, via the macrolide nitrogen having only the aglycone moiety, without sugar substituents either in C/3 or C/5 position, also possessing the earlier mentioned therapeutic action, have hitherto not been described.

DETAILED DESCRIPTION OF THE INVENTION

A characteristic of compounds represented by Formula I is selective accumulation in target organs and cells in the above mentioned inflammatory diseases and conditions. These pharmacokinetic properties enable the compounds represented by Formula I to act at the inflammation site in inflammation cells by inhibiting the production of inflammation mediators. In such a manner, the unfavourable systemic side-effects of corticosteroids or non-steroidal anti-inflammatory molecules are avoided and the therapeutic action of either the steroid or the NSAID moiety is targeted to the area where it is most needed. Following local or systemic application molecules rapidly accumulate in inflammation cells wherein they act by inhibiting the production of cytokines and chemokines and/or other inflammatory mediators thus suppressing the inflammation.

According to the known and established state of the art, compounds represented by Formula I, which are the object of the present invention, their pharmacologically acceptable salts, pharmaceutical compositions comprising them, and processes for making them have hitherto not been described. None of the compounds which are the object of the present invention has been described either as anti-inflammatory substance or as an inhibitor of eosinophilic accumulation in inflammation tissues.

In one aspect, the present invention relates to:

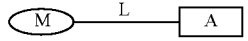

a) compounds represented by Formula I:

wherein M represents a macrolide subunit with substructure II:

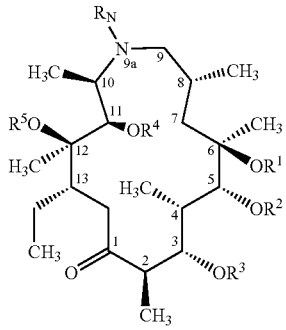

wherein
$R^1, R^2, R^3, R^4$ and $R^5$ are, independently of each other, hydrogen or groups such as $C_1$-$C_4$ alkyl (preferably methyl), alkanoyl (preferably acetyl), alkoxycarbonyl (preferably methoxycarbonyl or tert-butoxycarbonyl), arylmethoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl);

In another aspect $R^1, R^2, R^3, R^4$ and $R^5$ are independantly chosen from the group consisting of $C_1$-$C_4$ alkyl and hydrogen.

In another aspect $R^1, R^2, R^3, R^4$ and $R^5$ are independantly chosen from the group consisting of methyl and hydrogen.

$R_N$ represents the covalent link with $X^1$ of chain L;

L represents a linker chain with substructure III:

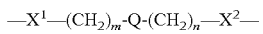

wherein
$X^1$ is —$CH_2$— or —$C(O)$—;
$X^2$ is —NH— or —O—;
Q is —NH— or —$CH_2$—;
m and n are, independently, integers from zero to 4;
with the proviso that if Q=NH, n cannot be zero;
In another aspect $X^1$ is $CH_2$ and $X^2$ is NH.

In another aspect of the invention m=1, n=1 and Q=$CH_2$

This definition of the linking group is preferred not only for conjugates of nonsteroids and macrolides of Formula II but for any conjugate within Formula I. Other linking groups can be used as long as they provide the necessary spacer and can serve to link one subunit of the Formula I with the other, as is well-known in the art. For example at U.S. Pat. No. 6,297,260, which is incorporated by reference in its entirety, at claim 1 and the specific list of NSAIDs contained therein.

D represents a nonsteroidal subunit derived from nonsteroidal anti-inflammatory drugs (NSAID) or a steroid subunit preferably a steroid of substructure IV:

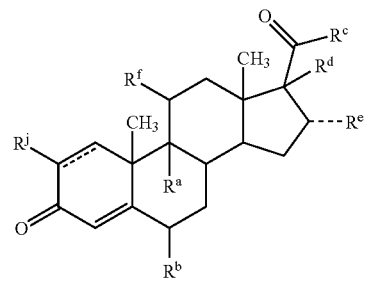

wherein
$R^a$, $R^b$, independently, are hydrogen or halogen;
$R^f$ is hydrogen, hydroxyl group or halogen (preferably chlorine) or forms a C=O (carbonyl) group with the carbon atom to which it is linked;
$R^c$ is the covalent link with $X^2$ of chain L;
$R^d$ and $R^e$, independently, are hydrogen, hydroxy, methyl or $C_1$-$C_4$ alkoxy (preferably methoxy or n-propoxy) or together with the pertaining C-atoms represent 1,3-dioxolane ring which can be additionally alkyl or alkenyl mono or di-substituted (preferably 2,2-dimethyl or 2-monopropyl or trans-propenyl ring)
$R^j$ is hydrogen or halogen (preferably chlorine).

In another aspect the present invention relates to compounds of Formula IV chosen from the group consisting of

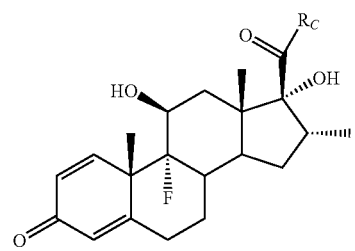

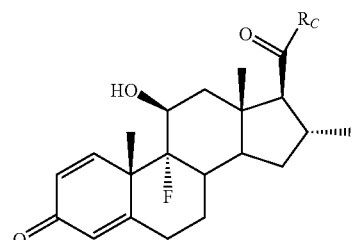

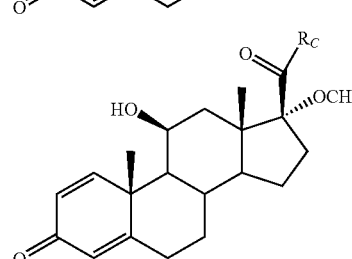

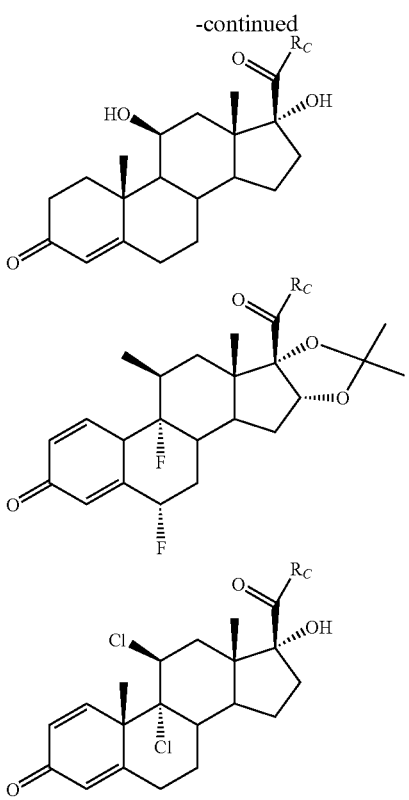

In another aspect, the present invention relates to processes for preparation of the foregoing compounds and to intermediates which may be used in such preparation.

In a third aspect, the present invention relates to combinations of one or more of the foregoing compounds in quantities sufficient for suppression of inflammatory processes; (e.g. two or more NSAID conjugates of the invention, two or more steroid conjugates of the invention, two or more compounds of the invention with at least one being an NSAID conjugate of the invention and at least one being a steroid conjugate of the invention.) These combinations offer more pronounced antiinflammatory activity if needed to treat inflamatory disease and conditions.

In yet an additional aspect, the present invention directed to methods for the use of the foregoing compounds in the treatment of disorders and conditions caused by inflammatory processes or to uses of the present compound in the treatment of the foregoing disorders or in the manufacture of medicaments for such treatment.

In yet another aspect of the invention pharmaceutical compositions comprising a compound of the invention and pharmaceutically acceptable salts or solvates thereof including pharmaceutically acceptable diluent or carrier are contemplated. Examples include but are not limited to carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethycellulose, hydroxyethylcellulose, ethylcellulose, methycellulose, polyvinyl alcohol, polyvinyl pyrolidone, N-vinylacetamide polymer, polyvinyl methacrylate, polyethylene glycol, pluronic, gelatin, methyl vinyl ether-maleic anhydride copolymer, starch, soluble starch croscaremlose, pullulan and a copolymer of methyl acrylate and 2-ethylhexyl acrylate lecithin, lecithin derivative, propylene glycol fatty acid esters, glycerin fatty acid esters, sorbitan fatty acid esters, polyoxyethylene sorbitan fatty acid esters, polyethylene glycol fatty acid esters polyoxyethylene hydrated castor oil, polyoxyethylene alkyl ethers, and pluronic. Appropriate buffer system if diluent is used is in pH range of 4 to 8, together with low molecular weight alcohols like thanol and isopropanol. The use of preservatives and masking agents is suitable.

In yet another aspect of the invention is a method of treatment of inflamatory diseases, disorders, and conditions characterized by or associated with an undesirable inflammatory immune response and all diseases and conditions induced by or associated with an excessive secretion of TNF-α and IL-1 which comprises administering to a subject a therapeutically effective amount of a compound of the invention.

In yet another aspect of the invention is a method of treating inflammatory conditions and immune or anaphylactic disorders associated with infiltration of leukocytes into inflamed tissues in a subject in need thereof which comprises administering to said subject a therapeutically effective amount of a compound of the invention.

In yet another aspect of the invention inflammatory conditions and immune disorders to be treated by the compounds of the invention are chosen from the group consisting of asthma, adult respiratory distress syndrome, bronchitis, cystic fibrosis, rheumatoid arthritis, rheumatoid spondylitis, osteoarthritis, gouty arthritis, uveitis, conjunctivitis, inflammatory bowel conditions, Crohn's disease, ulcerative colitis, distal proctitis, psoriasis, eczema, dermatitis, coronary infarct damage, chronic inflammation, endotoxin shock, and smooth muscle proliferation disorders.

In yet another aspect of the invention inflammatory conditions and immune disorders to be treated by the compounds of the invention are chosen from the group consisting of asthma, adult respiratory distress syndrome, chronic obstructive pulmonary diseases, inflammatory bowel conditions, Crohn's disease, bronchitis, and cystic fibrosis.

In yet another aspect of the invention is a method of treatment of inflammatory diseases, disorders and conditions characterized by or associated by excessive unregulated production of cytokines or Inflamatory mediators which comprises administering to a subject a therapeutically effective amount of a compound of the invention.

Symbols M, L and D represent three different subunits of compounds of Formula I. The symbol M represents the macrolide subunit, and the symbol D represents the steroid or nonsteroidal subunit linked through the chain L with the macrolide subunit M. In Formula I, D can represent a nonsteroidal anti-inflammatory subunit, i.e., a moiety of a nonsteroidal antiinflammatory drug (NSAID). Suitable NSAIDs include, but are not limited to, those which inhibit cyclooxygenase, the enzyme responsible for the biosyntheses of the prostaglandins and certain autocoid inhibitors, including inhibitors of the various isoenzymes of cyclooxygenase (including, but not limited to, cyclooxygenase-1 and -2), and as inhibitors of both cyclooxygenase and lipoxygenase relates to nonsteroidal anti-inflammatory drug (NSAID), such as the commercially available NSAIDs aceclofenac, acemetacin, acetaminophen, acetaminosalol, acetyl-salicylic acid, acetyl-salicylic-2-amino-4-picoline-acid, 5-aminoacetylsalicylic acid, alclofenac, aminoprofen, amfenac, ampyrone, ampiroxicam, anileridine, bendazac, benoxaprofen, bermoprofen, α-bisabolol, bromfenac, 5-bromosalicylic acid acetate, bromosaligenin, bucloxic acid, butibufen, carprofen, celecoxib, chromoglycate, cinmetacin, clindanac, clopirac, sodium diclofenac, diflunisal, ditazol, droxicam, enfenamic acid, etodolac, etofenamate, felbinac, fenbufen, fenclozic acid, fendosal, fenoprofen, fentiazac, fepradinol, flufenac, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lornoxicam, loxoprofen, meclofenamic acid, mefenamic acid, meloxicam, mesalamine, metiazinic acid, mofezolac, montelukast, mycophenolic acid, nabumetone, naproxen, niflumic acid, nimesulide, olsalazine, oxaceprol, oxaprozin, oxyphenbutazone, paracetamol, parsalmide, perisoxal, phenyl-acetyl-salicylate, phenylbutazone, phenylsalicylate, pyrazolac, piroxicam, pirprofen, pranoprofen, protizinic acid, reserveratol, salacetamide, salicylamide, salicylamide-O-acetyl acid, salicylsulphuric acid, salicin, salicylamide, salsalate, sulindac, suprofen, suxibutazone, tamoxifen, tenoxicam, theophylline, tiaprofenic acid, tiaramide, ticlopridine, tinoridine, tolfenamic acid, tolmetin, tropesin, xenbucin, ximoprofen, zaltoprofen, zomepirac, tomoxiprol, zafirlukast and cyclosporine. Additional NSAID genera and particular NSAID compounds are disclosed in U.S. Pat. No. 6,297,260, incorporated entirely by reference (especially in the generic formulas of its claim 1 and the recitation of specific list of NSAID's contained therein and in claim 3, and thiazulidene NSAIDs disclosed in International Patent Application WO 01/87890, incorporated herein by reference in its entirety. Preferred are indomethacin, flufenamic acid, flunixin and theophylline. Most preferred is indomethacin. In certain embodiments, the NSAID subunit is neither acetyl salicylic acid nor mycophenolic acid.

In formula I D may also represent a steroid subunit including, but not limited to, corticosteroids (such as glucocorticoids and mineralocorticoids) and androgens. Non-limiting examples of corticosteroids include cortisol, cortisone, clobetasol, hydrocortisone, fludrocortisone, fludroxycortide, flumetasone, flunisolide, fluocinolone, fluocinonide, fluocortolone, fluorometholone, prednisone, prednisolone, 6-alpha-methylprednisolone, triamcinolone, alclometasone, beclometasone, betamethasone, budesonide, dexamethasone, amcinonide, cortivazol, desonide, desoximethasone diflucortolone, difluprednate, fluclorolone and dichlorisone, fluperinidene, fluticasone, halcinonide, meprednisone, methylprednisolone, paramethasone, prednazoline, prednylidene, tixocortol, triamcinolone, and acid derivatives thereof, e.g., acetate, propionate, dipropionate, valerate, phosphate, isonicotinate, metasulfobenzoate, tebutate, and hemisuccinate).

Unless stated otherwise, the following terms have the meanings ascribed to them below.

"Halogen" means a halogen atom which may preferably be: fluorine, chlorine or bromine (the most preferably fluorine or chlorine).

"Alkyl" means a linear or branched saturated monovalent hydrocarbon radical of one to ten carbon atoms, more preferably one to six carbon atoms The preferred straight-chain or branched-chain alkyls include methyl, ethyl, propyl, iso-propyl, butyl, sec-butyl and tert-butyl. $C_1$-$C_4$ alkyl is prefered. Methyl is most preferred. Alkyl groups may be substituted with one up to five substituents including halogen (preferably fluorine or chlorine), hydroxy, alkoxy (preferably methoxy or ethoxy), acyl, acylamino cyano, amino, N-($C_1$-$C_4$)alkylamino (preferably N-methylamino or N-ethylamino), N,N-di($C_1$-$C_4$-alkyl)amino (preferably dimethylamino or diethylamino), aryl (preferably phenyl) or heteroaryl, thiocarbonylamino, acyloxy, amino, amidino, alkylamidino, thioamidino, aminoacyl, aminocarbonylamino, aminothiocarbonylamino, aminocarbonyloxy, aryl, heteroaryl, aryloxy, aryloxyaryl, nitro, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, cycloalkyl, cycloalkoxy, heteroaryloxy, heterocyclyloxy, and oxycarbonylamino. Such substituted alkyl groups are within the present definition of "alkyl." The present definition of alkyl carries over to other groups having an alkyl moiety such as alkoxy or alkanoyl.

"Alkenyl" means a linear or branched monovalent hydrocarbon radical of two to ten and preferably two to six carbon atoms which has at least one double carbon-carbon bond. Alkenyl groups may be substituted with the same groups as alkyl and such optionally substituted alkenyl groups are encompassed within the term "alkenyl". Ethenyl, propenyl, butenyl and cyclohexenyl are preferred.

"Alkynyl" means a linear or branched monovalent hydrocarbon radical, having a straight-chain or a branched-chain of two to ten, and preferably two to six carbon atoms and containing at least one and preferably no more than three triple carbon-carbon bonds. Alkynyl groups can be substituted with the same groups as alkyl, and the substituted groups are within the present definition of alkynyl. Ethynyl, propynyl and butynyl groups are preferred.

"Cycloalkyl" means a cyclic group having 3-8 carbon atoms having a single ring optionally fused to an aryl or heteroaryl group. The cycloalkyl groups can be substituted as specified for "aryl" below, and the substituted cycloalkyl groups are within the present definition of "cycloalkyl". Preferred cycloalkyls are cyclopentyl and cyclohexyl.

"Aryl" means an unsaturated aromatic carbocyclic group having 6-14 carbon atoms having a single ring such as phenyl or multiple fused rings such as naphthyl. Aryl may optionally be further fused to an aliphatic or aryl group or can be substituted with one or more substituents such as halogen (fluorine, chlorine and/or bromine), hydroxy, $C_1$-$C_7$ alkyl, $C_1$-$C_7$ alkoxy or aryloxy, $C_1$-$C_7$ alkylthio or arylthio, alkylsulfonyl, cyano or primary or nonprimary amino.

"Heteroaryl" means a monocyclic or a bicyclic aromatic hydrocarbon ring having from 2 to 10 carbon atoms and from 1 to 4 heteroatoms, such as O, S or N. The heteroaryl ring may optionally be fused to another heteroaryl, aryl or aliphatic cyclic group. Examples of this type are furan, thiophene, imidazole, indole, pyridine, oxazole, thiazole, pyrrole, pyrazole, tetrazole, pyrimidine, pyrazine and triazine, with furan, pyrrole, pyridine and indole being preferred. The term includes groups that are substituted with the same substituents as specified for aryl above.

"Heterocyclic" means a saturated or unsaturated group having a single or multiple rings and from 1 to 10 carbon atoms and from 1-4 heteroatoms selected from nitrogen, sulfur or oxygen, wherein in a fused ring system the other ring or rings can be aryl or heteroaryl. Heterocyclic groups can be substituted as specified for alkyl groups and the thus substituted heterocyclic groups are within the present definition.

When $R^c$ represents a covalent link, the nonsteroidal or steroid subunit D is linked via $R^c$ with the chain L to the macrolide subunit M.

When $R_N$ represents a covalent bond, the macrolide subunit M is linked via $R_N$ with the chain L to the nonsteroidal or steroid subunit D.

In the preparation of the compounds represented by Formula I of the specified pharmacological activity, in the present invention certain new compounds were prepared as intermediates in the preparation of pharmacologically active compounds. The present invention also relates to such intermediates.

The term "salts" can include acid addition salts or addition salts of free bases. Examples of acids which may be employed to form pharmaceutically acceptable acid addition salts include but are not limited to salts derived from nontoxic inorganic acids such as nitric, phosphoric, sulfuric, or hydrobromic, hydroiodic, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, maleic, succinic, or citric acids. Non-limiting examples of such salts include napadisylate, besylate, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al. "Pharmaceutical Salts," J. of Pharma. Sci., 1977; 66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. However, since memantine is highly soluble, aqueous solutions are preferred. Suitable pharmaceutical carriers are described in "Remington's Pharmaceutical Sciences" by E. W. Martin, 18th Edition. Particularly preferred for the present invention are carriers suitable for immediate-release, i.e., release of most or all of the active ingredient over a short period of time, such as 60 minutes or less, and make rapid absorption of the drug possible.

The present invention also encompasses solvates (preferably hydrates) formed by the compounds represented by Formula I or their salts.

The present invention also relates to all possible tautomeric forms which can be formed by individual compounds of Formula I.

The present invention also encompasses prodrugs of Formula I compounds, i.e., compounds which release an active parent drug according to Formula (I) in vivo when administered to a mammalian subject. Prodrugs of a compound of Formula I are prepared by modifying functional groups present in the compound of Formula I in such a way that the modifications may be cleaved in vivo to release the parent compound. Prodrugs include compounds of Formula I wherein a hydroxy, amino, or carboxy group of a Formula I compound is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds of Formula I.

The compounds of Formula I have one or more chirality centers and, depending on the nature of individual substituents, they can also have geometrical isomers. Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has a chiral center, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomer respectively). A chiral compound can exist as either an individual enantiomer or as a mixture of enantiomers. A mixture containing equal proportions of the enantiomers is called a "racemic mixture". The present invention encompasses all individual isomers of compounds of Formula I. The description or naming of a particular compound in the specification and claims is intended to include both individual enantiomers and mixtures, racemic or otherwise, thereof. Methods for the determination of stereochemistry and the separation of stereoisomers are well-known in the art.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

"Treating" or "treatment" of a state, disorder or condition includes:

(1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or
(3) relieving the disease, i.e., causing regression of the state, disorder or condition or at least one of its clinical or subclinical symptoms.

The benefit to a subject to be treated is either statically significant or at least perceptible to the patient or to the physician A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The four classic symptoms of acute inflammation are redness, elevated temperature.

Swelling, and pain in the affected area, and loss of function of the affected organ.

Symptoms and signs of inflammation associated with specific conditions include:

rheumatoid arthritis—pain, swelling, warmth and tenderness of the involved joints;
generalized and morning stiffness;
insulin-dependent diabetes mellitus—insulitis; this condition can lead to a variety of complications with an inflammatory component, including: retinopathy, neuropathy, nephropathy; coronary artery disease, peripheral vascular disease, and cerebrovascular disease;
autoimmune thyroiditis—weakness, constipation, shortness of breath, puffiness of the face, hands and feet, peripheral edema, bradycardia;
multiple sclerosis—spasticity, blurry vision, vertigo, limb weakness, paresthesias;
uveoretinitis—decreased night vision, loss of peripheral vision;
lupus erythematosus—joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis;
scleroderma—Raynaud's disease; swelling of the hands, arms, legs and face; skin thickening; pain, swelling and stiffness of the fingers and knees, gastrointestinal dysfunction, restrictive lung disease; pericarditis; renal failure,
other arthritic conditions having an inflammatory component such as rheumatoid spondylitis, osteoarthritis, septic arthritis and polyarthritis—fever, pain, swelling, tenderness;
other inflammatory brain disorders, such as meningitis, Alzheimer's disease, AIDS dementia encephalitis—photophobia, cognitive dysfunction, memory loss;
other inflammatory eye inflammations, such as retinitis—decreased visual acuity;
inflammatory skin disorders, such as, eczema, other dermatites (e.g., atopic, contact), psoriasis, burns induced by UV radiation (sun rays and similar UV sources)—erythema, pain, scaling, swelling, tenderness;
inflammatory bowel disease, such as Crohn's disease, ulcerative colitis—pain, diarrhea, rectal bleeding, fever, arthritis;
asthma—shortness of breath, wheezing;
other allergy disorders, such as allergic rhinitis—sneezing, itching, runny nose conditions associated with acute trauma such as cerebral injury following stroke—sensory loss, motor loss, cognitive loss;
heart tissue injury due to myocardial ischemia—pain, shortness of breath;
lung injury such as that which occurs in adult respiratory distress syndrome—shortness of breath, hyperventilation, decreased oxygenation, pulmonary infiltrates;
inflammation accompanying infection, such as sepsis, septic shock, toxic shock syndrome—fever, respiratory failure, tachycardia, hypotension, leukocytosis;
other inflammatory conditions associated with particular organs or tissues, such as nephritis (e.g., glomerulonephritis)-oliguria, abnormal urinalysis;
inflamed appendix—fever, pain, tenderness, leukocytosis;
gout—pain, tenderness, swelling and erythema of the involved joint, elevated serum and/or urinary uric acid;
inflamed gall bladder—abdominal pain and tenderness, fever, nausea, leukocytosis;
chronic obstructive pulmonary disease—shortness of breath, wheezing;
congestive heart failure—shortness of breath, rales, peripheral edema;
Type II diabetes—end organ complications including cardiovascular, ocular, renal, and peripheral vascular disease
lung fibrosis—hyperventilation, shortness of breath, decreased oxygenation;
vascular disease, such as atherosclerosis and restenosis—pain, loss of sensation, diminished pulses, loss of function
and alloimmunity leading to transplant rejection—pain, tenderness, fever.

Subclinical symptoms include without limitation diagnostic markers for inflammation the appearance of which may precede the manifestation of clinical symptoms. One class of subclinical symptoms is immunological symptoms, such as the invasion or accumulation in an organ or tissue of proinflammatory lymphoid cells or the presence locally or peripherally of activated pro-inflammatory lymphoid cells recognizing a pathogen or an antigen specific to the organ or tissue. Activation of lymphoid cells can be measured by techniques known in the art.

"Delivering" a therapeutically effective amount of an active ingredient to a particular location within a host means causing a therapeutically effective blood concentration of the active ingredient at the particular location. This can be accomplished, e.g., by local or by systemic administration of the active ingredient to the host.

The term host or subject in need thereof as used herein refers to a mammal preferably a human.

The term leaving group refers to a chemical group which is capable of being displaced by a nucleophile. Examples of such groups include but are not limited to halogen, mesylate, tosylate and ester groups.

Methods of Preparation

A further aspect of the present invention relates to a method for the preparation of compounds within Formula I comprising:

a) for the compounds of Formula I, wherein $X^2$ is —NH—a reaction of the steroid or nonsteroidal subunit of the substructure V:

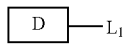

V (wherein L₁ represents a leaving group such as hydroxy)
and the amino group of the macrolide subunit of the substructure VIa:

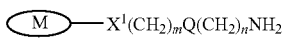

VIa for the compounds of Formula I, wherein $X^2$ represents —O—;

a reaction of the steroid or nonsteroidal subunit of the substructure V
(wherein L₁ represents a leaving group such as hydroxy, and the hydroxyl group of the macrolide subunit of the substructure VIb:

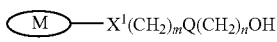

VIb

Methods of Preparation:

a) A compound within Formula I is prepared by a reaction of a carboxylic acid of the steroid or nonsteroidal subunit of the substructure V and the amino group of the macrolide subunit of the substructure VIa whereby the amide linkage is effected, and using the usual derivatives having an activating effect on carboxylic acid such as mixed anhydrides, especially carbodiimides or benzotriazole. The reaction proceeds in the presence of a base (preferably an organic base), e.g. triethylamine, at room temperature under an inert atmosphere, e.g. a nitrogen or argon blanket, over a period from several hours to several days.

Steroid or nonsteroidal subunits of the substructure V are either commercially available products or have been obtained, like the starting macrolide subunits of the substructure VIa by methods for preparation of analogous compounds described in our earlier patent applications (HR Patent Application No. 20010018; WO Patent Application No. 02/055531); WO 04/005309; WO 04/005310 herein incorporated by reference in their entireties.

The reaction is generally performed with acid derivatives which have the ability to activate the carboxylic acid group of steroidal anti-inflammatory subunit, such as halogenides, mixed anhydrides and especially carbodiimides (such as -(3-dimethylaminopropyl)-3-ethyl-carbodiimide (EDC)) and benzotriazoles. The reaction proceeds in the presence of a base, such as an organic base (e.g., triethylamine), at room temperature under an inert atmosphere such as nitrogen or argon. The reaction may require several hours to several days to come to completion.

For example, when L is —K—NH— (wherein K is the portion of the L molecule attached to the macrolide) the compound of Formula I can be formed by derivatizing an NH group on the macrolide ring to an —N—K—(NH₂)— group and reacting the derivatized macrolide with a steroid or nonsteroidal anti-inflammatory subunit represented by Formula V:

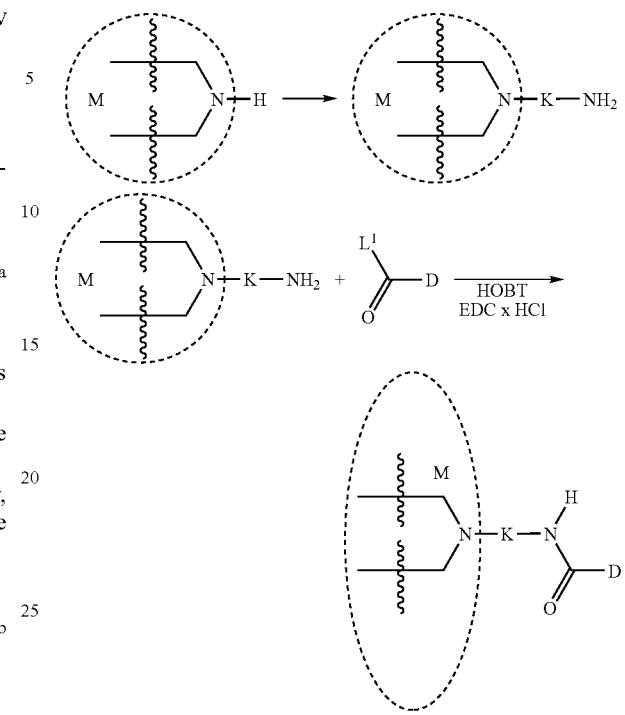

b) Preparation of a compound of Formula I is carried out by a reaction of the carboxylic acid of the steroid or nonsteroidal subunit of the substructure V and the hydroxyl group of the macrolide subunit of the substructure VIb whereby the ester bond is formed, and the reaction proceeds by using carboxylic acid activating agents such as mixed anhydrides, especially carbodiimides. The reaction proceeds at low temperatures (preferably –5° C.) under an inert atmosphere, e.g. nitrogen or argon blanket, over the period from several hours to several days.

Starting macrolide subunits of the substructure VIb are compounds described in the literature or can be prepared by the procedures described for the preparation of analogous compounds (Costa, A. M. et al., *Tetrahedron Letters* 2000, 41, 3371-3375). For example, the reaction of an alkenoyl derivative having the formula $CH_2=CH(CH_2)_mC(O)O$-alkyl (preferably methylacrylate) with the secondary nitrogen atom of the macrolide subunit, yields a chain having an ester group at its end. The ester group is then reduced with a metal hydride (preferably LiAlH₄) in an anhydrous organic solvent at a lower temperature (preferably 0° C.) to yield an alcohol derivative of the substructure VIb.

For example, when linkage L is —K—O—, the compound of Formula I can be formed by (1) derivatizing an NH group on a macrolide to an N—K—OH group and (2) reacting the derivatized macrolide with the free carboxylic acid group on a steroid or nonsteroidal subunit

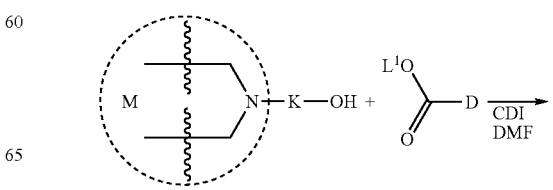

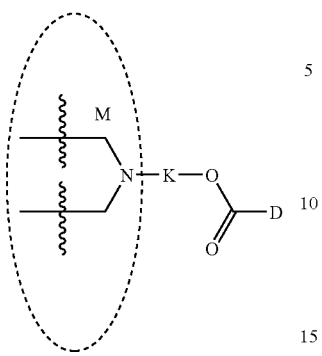

The non-steroidal anti-inflammatory subunit D may contain a —C(O)L$^1$ group (such as a free carboxylic acid group) or be derivatized by methods known in the art.

Scheme I

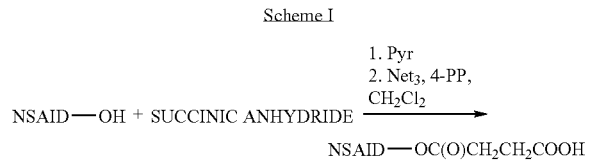

According to Scheme I, NSAID compounds having a hydroxyl group may alternatively be derivatized by the action of succinic anhydride in the presence of pyridine followed by reaction of the intermediate so produced with triethylamine, 4-pyrrolopyridine in methylene chloride to produce NSAID having free carboxylic acid group (Huang C. M. et al. Chem. & Biol. 2000, 7, 453-461, Hess S. et al. Bioorg. & Med. Chem. 2001, 9, 1279-1291) The NSAID derivatives so produced may be coupled either to a linker macrolide compound such as formula VIa or VIb.

Scheme II

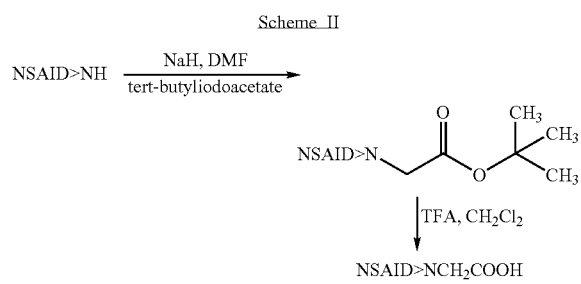

According to Scheme II, NSAID compounds having an amino group may alternatively be derivatized by the action of sodium hydride and tert-butyliodoacetate in N,N-dimethylformamide to produce a (butoxy carbonyl derivative of the NSAID which is then reacted with (trifluoracetic acid in methylene chloride to produce NSAID having free carboxylic acid group (Hess S. et al. Bioorg. & Med. Chem. 2001, 9, 1279-1291). The NSAID derivatives so produced may be coupled either to a linker macrolide compound such as formula VIa or VIb.

Scheme III

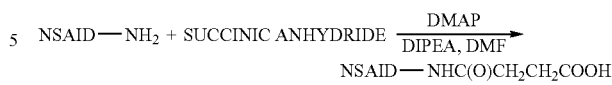

NSAID—NHC(O)CH$_2$CH$_2$COOH

Alternatively by NSAID compounds having an amino group may be derivatized according to Scheme III by the action of succinic anhydride in the presence of dimethylaminopyridine, N,N'-diisopropylethylamine in dimethylformamide to produce NSAID having free carboxylic acid group (Pandori M. W. et al. Chem. & Biol. 2002, 9, 567-573). The NSAID derivatives so produced may be coupled either to a linker macrolide compound such as formula VIa or VIb.

Compounds of Formula I can generally be obtained so that: one end of the chain L is first linked to the macrolide subunit M, and then the other end of the chain is linked to the non-steroidal or steroid subunit D; or one a of the chain L is first linked to the nonsteroidal or steroid subunit D and then the other end of the chain is linked to the macrolide subunit M, and, finally, one end of the yet unformed chain is linked to the macrolide subunit M, and the other end of the also unformed chain is linked to the nonsteroidal or steroid subunit D, and subsequently the ends are chemically linked to form the chain L.

To prevent undesirable side-reactions, it is frequently necessary to protect certain groups such as e.g. a hydroxy or amino group. A comprehensive discussion of the ways in which such groups may be protected and methods for cleaving the resulting protected derivatives is given by for example T. W. Greene and P. G. M Wuts in Protective Groups in Organic Synthesis 2$^{nd}$ ed., John Wiley & Son, Inc 1991 and by P. J. Kocienski in Protecting Groups, Georg Thieme Verlag 1994 which are incorporated herein by reference. Examples of suitable amino protecting groups include acyl type protecting groups (e.g. formyl, trifluoroacetyl and acetyl), aromatic urethane type protecting groups (e.g. benzyloxycarbonyl (Cbz) and substituted Cbz, and 9-fluorenylmethoxycarbonyl (Fmoc)), aliphatic urethane protecting groups (e.g. t-butyloxycarbonyl (Boc), isopropyloxycarbonyl and cyclohexyloxycarbonyl) and alkyl type protecting groups (e.g. benzyl, trityl and chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate. Hydroxy groups may be protected by reaction of for example acetic anhydride, benzoic anhydride or a trialkylsilyl chloride in an aprotic solvent. Examples of aprotic solvents are dichloromethane, N,N-dimethylformamide, dimethylsulfoxide, tetrahydrofuran and the like.

For example, one possibility for the protection of the amino group is phthalimide. Deprotection using hydrazine is described in the examples.

Corresponding protection for amino and alkylamino groups are groups such as alkanoyl (acetyl), alkoxycarbonyl (methoxycarbonyl, etoxycarbonyl or tert-butoxycarbonyl), arylmethoxycarbonyl (benzyloxycarbonyl), aroyl (benzoyl) and alkylsilyl group (trimethylsilyl or trimethylsilyletoxymethyl). The conditions for elimination of the protective group depend on the selection and properties of that group. Thus, for example, acyl groups such as alkanoyl, alkoxycarbonyl and aroyl group can be removed by hydrolysis in the presence of a base (sodium or potassium hydroxide), tert-butoxycarbonyl or alkylsilyl (trimethylsilyl) group can be removed with a corresponding acid (for example, hydrochloric, sulphuric, phosphoric or trifluoroacetic acid), while arylmethoxycarbonyl group (benzyloxycarbonyl) can be removed by hydrogenolysis in the presence of a catalyst such as palladium-on-charcoal.

A further aspect of the present invention relates to the methods for using the compounds of Formula I as anti-inflammatory, anti-anaphylactic and immunomodulating agents which can be administered in different ways, depending on the inflammation site, e.g. percutaneously, orally, buccally, rectally, parenterally or by inhalation when application within the respiratory tract is intended.

A further aspect of the present invention relates to the methods for using the compounds of Formula I as anti-inflammatory, anti-anaphylactic and immunomodulating agents which can be administered in different ways, depending on the inflammation site. Further, the present invention relates to pharmaceutical compositions containing an effective dose of compounds of the present invention as well as pharmaceutically acceptable excipients, such as carriers or diluents.

The preparation of the pharmaceutical compositions of the invention can include mixing, granulating, tabletting and dissolving the ingredients. Chemical carriers can be in solid or liquid form. Solid carriers can be lactose, sucrose, talc, gelatine, agar, pectin, magnesium stearate, fatty acids without limitation. Liquid carriers can be syrups, oils such as olive, sunflower seed or soybean oils, water, or physiologic saline without limitation. Similarly, carriers may also contain a component for a sustained release of the active component such as glyceryl monostearate or glyceryl distearate. Several forms of pharmaceutical compositions can be prepared. If a solid carrier is used, these forms can include tablets, caplets, solid gelatinous capsules, powders or granules without limitation that can be administered orally. The amount of the solid carrier can vary but mainly it is in the range from 25 mg to 1 g. If a liquid carrier is used, the formulation can be in the form of a syrup, emulsion, soft gelatinous capsules, or sterile injectable liquids, or nonaqueous liquid suspensions topically or systemically, e.g., orally, parenterally, percutaneously, mucosally, e.g., buccally, intranasally, intrarectally and intravaginally. "Parenterally" means by intravenous, intramuscular or subcutaneous route. The corresponding preparations of the compounds of the present invention can be used in the prophylaxis as well as in the therapeutic treatment (prevention, delay, inhibition or relief) of several disorders (diseases and other pathological inflammatory conditions) caused by or associated with an abnormal or undesirable (excessive, non-regulated, or dysregulated) inflammatory immune response involving the production of inflammatory cytokines or other inflammation mediators, including without limitation TNF-$\alpha$ and IL-$\beta$. These disorders include autoimmune diseases such as rheumatoid arthritis, insulin-dependent diabetes mellitus, autoimmune thyroiditis, multiple sclerosis, uveoretinitis, lupus erythematosus, scleroderma; other arthritic conditions having an inflammatory component such as rheumatoid spondylitis, osteoarthritis, septic arthritis and polyarthritis; other inflammatory brain disorders, such as meningitis, Alzheimer's disease, AIDS dementia encephalitis, other inflammatory eye inflammations, such as retinitis; inflammatory skin disorders, such as, eczema, other dermatites (e.g., atopic, contact), psoriasis, burns induced by UV radiation (sun rays and similar UV sources); inflammatory bowel disease, such as Crohn's disease, ulcerative colitis; asthma; other allergy disorders, such as allergic rhinitis; conditions associated with acute trauma such as cerebral injury following stroke, heart tissue injury due to myocardial ischemia, lung injury such as that which occurs in adult respiratory distress syndrome; inflammation accompanying infection, such as sepsis, septic shock, toxic shock syndrome, other inflammatory conditions associated with particular organs or tissues, such as nephritis (e.g., glomerulonephritis), inflamed appendix, gout, inflamed gall bladder, chronic obstructive pulmonary disease, congestive heart failure, Type II diabetes, lung fibrosis, vascular disease, such as atherosclerosis and restenosis; and alloimmunity leading to transplant rejection. The compounds can also be administered by inhalation when application within the respiratory tract is intended. A further object of the present invention relates to the preparation of various pharmaceutical forms of the compounds to achieve the optimal bioavailability of the active compound of Formula I.

For percutaneous or mucosal external administration, the compound of Formula I can be prepared in a form of an ointment or cream, gel or lotion. Ointments, creams and gels can be formulated using a water or oil base with addition of an appropriate emulsifier or gelling agent Formulation of the present compounds is especially significant for respiratory inhalation, wherein the compound of Formula I is to be delivered in the form of an aerosol under pressure. It is preferred to micronize the compound of Formula I after it has been homogenised, e.g., in lactose, glucose, higher fatty acids, sodium salt of dioctylsulfosuccinic acid or, most preferably, in carboxymethyl cellulose, in order to achieve a microparticle size of 5 µm or less for the majority of particles. For the inhalation formulation, the aerosol can be mixed with a gas or a liquid propellant for dispensing the active substance. An inhaler or atomizer or nebulizer may be used. Such devices are known. See, e.g., Newman et al., *Thorax*, 1985, 40:61-676 Berenberg, M., *J. Asthma USA*, 1985, 22:87-92. A Bird nebulizer can also be used. See also U.S. Pat. Nos. 6,402,733; 6,273,086; and 6,228,346.

The compound of the structure I for inhalation is preferably formatted in the form of a dry powder with micronized particles, as described herein.

The compound can also be incorporated into a formulation for treating inflammation localized in an organ or tissue, e.g., Crohn's disease, where it can be administered orally or rectally. Formulations for oral administration can incorporate excipients enabling bioavailability of the compound at the site of inflammation. This can be achieved by different combinations of enteric and delayed release formulations. The compound of Formula I can also be used in the treatment of Crohn's disease and intestinal inflammation disease if the compound is applied in the form of a clyster, for which a suitable formulation can be used, as is well known in the field.

A therapeutically effective amount of the compound of the present invention can be determined by methods known in the art. Since the compound of the present invention is more efficiently delivered to the desired site than the corresponding anti-inflammatory steroid or NSAID drug alone, a lesser amount of the compound on a molar basis than of the steroid or NSAED anti-inflammatory drug can be administered while still achieving the same therapeutic effect. Furthermore, since administration of the compound results in fewer side effects than with the corresponding steroid or NSAID anti-inflammatory drug, the steroid or NSAID amount can be increased. Thus, the table below serves only as a guide. A threshold therapeutically effective amount of the compound, a pharmaceutically salt thereof, a solvate thereof, or a prodrug thereof is generally equal to or less than a therapeutically effective amount of the nonsteroidal anti-inflammatory drug on a molar basis. Broad and preferred effective amounts of the compound, a pharmaceutically salt thereof, a solvate thereof, or a prodrug thereof are shown in the table below.

|  | Amount of Compound, Pharmaceutically Accetable Salt Thereof, Solvate Thereof, or Prodrug Thereof | |
| --- | --- | --- |
|  | mg/kg body weight/day of the steroid of NSAID (had it been administered alone) | µmol/kg body weight/day of the hybrid or the steroid or NSAID |
| Broad | from about 0.001 to about 1000 | from about 0.004 to about 4000 |
| Preferred | from about 0.01 to about 100 | from about 0.04 to about 400 |
| More Preferred | from about 1 to about 100 | from about 4 to about 400 |
| Most Preferred | from about 3 to about 30 | from about 12 to about 120 |

For example, if the preferred amount range for prednisone is 1-50 mg/day, this corresponds to a range of 2.79 µmol to 139.5 µmol per day. The starting amount range for a hybrid steroid-macrolide conjugate according to the invention will be also 2.79 µmol to 139.5 µmol of conjugate per day. This dosage can be fine-tuned in light of the present specification using the ordinary skill in the act.

The efficacy of the present compounds can be assessed by any method for assessing inflammation or anti-inflammatory effect. There are many known methods for this purpose including without limitation use of contrast ultrasound in conjunction with injection of microbubbles, measurement of inflammatory cytokines (such as TNF-α, IL-1, IFN-γ) measurement of activated immune system cells (activated T cells, cytotoxic T cells specifically recognizing the inflamed or transplanted tissue) as well as by observation (reduction of oedema reduction of erythema, reduction of pruritus or burning sensation, reduction of body temperature, improvement in function of the afflicted organ) as well as any of the methods provided below as well as any of the methods provided below.

The therapeutic effect of compounds of the present invention was determined in in vitro and in vivo experiments such as the following.

The beneficial antiinflammatory effect of the compounds of the present invention was determined in the following in vitro and in vivo experiments:

Formulations for oral administration can be so designed to enable bioavailability of the compound at the site of inflammation in the intestines. This can be achieved by different combinations of delayed release formulations. The compound of Formula I can also be used in the treatment of Crohn's disease and intestinal inflammation disease if the compound is applied in the form of an enema, for which a suitable formulation can be used.

The corresponding preparations of the compounds of the present invention can be used in the prophylaxis (including without limitation the prevention, delay or inhibition of recurrence of one or more of the clinical or subclinical symptoms discussed and defined in connection with the definitions of "treatment" above as well as in the therapeutic treatment of several diseases and and pathological inflammatory conditions including: asthma, chronic obstructive pulmonary disease, inflammatory nasal diseases such as allergic rhinitis, nasal polyps, intestinal diseases such as Crohn's disease, colitis, intestinal inflammation, ulcerative colitis, dermatological inflammations such as eczema, psoriasis, allergic dermatitis, neurodermatitis, pruritus, conjunctivitis and rheumatoid arthritis.

The biological effect of the compounds of the present invention was determined in the following in vitro and in vivo experiments:

Assay of Binding to Human Glucocorticoid Receptor

The gene for the alpha isoform of human glucocorticoid receptor was cloned by reverse polymerase chain reaction. The total RNA was isolated from human peripheral blood lymphocytes according to the instructions of the manufacturer (Qiagen), transcribed into cDNA with AMV reverse transcriptase (Roche) and the gene was multiplied by specific primers 1) 5'ATATGGATCCCTGATGGACTCCAAA-GAATCATTAACTCC3' [SEQ ID NO:1] and 2) 5'ATAT-CTCGAGGGCAGTCACTTTTGATGAAACAGAAG3' [SEQ ID NO:1]. The reaction product obtained was cloned into the XhoI/BamHI site of Bluescript KS plasmid (Stratagene), subjected to sequencing by the dideoxy fluorescent method with M13 and M13rev primers (Microsynth) and then it was cloned into the XhoI/BamHI site of pcDNA3.1 Hygro (+)plazmid (Invitrogen). $1 \times 10^5$ COS-1 cells were seeded onto a 12-well plate (Falcon) in DMEM medium (Life Technologies) with 10% FBS (Biowhitaker) and cultivated to a 70% confluence at 37° C. in an atmosphere with 5% $CO_2$. The medium was removed and 1 µg of DNA, 7 µl of PLUS reagent and 2 µl of Lipofectamin (Life Technologies) in 500 µl of DMEM were added per well. The cells were incubated at 37° C. in an atmosphere with 5% $CO_2$ and after 5 hours the same volume of 20% FBS/DMEM was added. After 24 hours, the medium was completely changed. 48 hours after transfection, the test compounds in different concentrations and 24 nM [$^3$H]dexamethazone (Pharmacia) in DMEM medium were added. The cells were incubated for 90 minutes at 37° C. in an atmosphere with 5% $CO_2$, washed three times with PBS buffer (Sigma) cooled to 4° C. (pH=7.4), and then lysed in Tris buffer (pH=8.0) (Sigma) with 0.2% of SDS (Sigma). After the addition of UltimaGold XR (Packard) scintillation liquid, the residual radioactivity was read in a Tricarb (Packard) β-scintillation counter.

Compounds 1 and 2 have the affinity for glucocorticoid receptor since in the assay they displace radioactive dexamethasone from the glucocorticoid receptor.

Assay of Inhibition of Mouse T-cell Hybridoma 13 Proliferation as a Result of Apoptosis Induction In a 96-well plate, triplicates of test steroid dilution in RPMI medium (Institute of Immunology, Zagreb) with 10% FBS were performed. To the solutions of compounds, 20000 cells per well were added and incubated overnight at 37° C. in an atmosphere with 5% $CO_2$, then 1 µCi of [$^3$H]thymidine (Pharmacia) was added and the mixture was incubated for additional 3 hours. The cells were harvested by applying a vacuum over GF/C filter (Packard). Onto each well, 30 µl of Microscynt O scintillation liquid (Packard) was added and the incorporated radioactivity was measured on a α-scintillation counter (Packard). The specificity of apoptosis induction by glucocorticoids was proven by antagonizing the proliferation inhibition with mifepristone (Sigma).

Compounds 1-5, 6 and 8 exhibit inhibition of T-cell hybridoma 13 proliferation in the concentrations from 1 µM to 1 nM.

Measurement of the Inhibition of Interleukin 4, Interleukin 5 and Interferon Production by γ Concanavalin-A Induced Murine Splenocytes Splenocytes were isolated from the spleen of Balb/C mice sacrificed by thiopental injection (Pliva). Spleens were chopped and mononuclear cells separated on Histopaque 1083 (Sigma Diagnostics, Cat. No 1083-1). Into a 96-well plate, compounds diluted in RPMI medium (Institute of Immunology) were pipetted with 10% foetal bovine serum (Biowhittaker) and cells (200000 per well) in the same medium, and concanavalin-A stimulator (Sigma cat No C5275) at the final concentration of 5 µg/ml were added. Positive control, in place of the dilution of compounds, consisted of RPMI medium with 10% foetal bovine serum and concanavalin-A in the same concentration of. Cells were incubated for 72 hours at 37° C., 95% humidity and in an atmosphere with 5% $CO_2$. Until determination of cytokines, the cells were frozen at −70° C.

Cytokines interleukin 4, interleukin 5 and interferon γ were determined by the specific ELISA method, according to manufacturer's recommendations (R&D).

Inhibition (as percentage) was calculated using the following formula:

% $inh$=(1-concentration of cytokines in sample/concentration of cytokins in positive control)*100

Compounds 1-5, 6 and 8 inhibit the production of cytokines in concentrations from 1 µM to 1 nM.

Model of Lung Eosinophilia in Mice

Male Balb/C mice with a body weight of 20-25 g were randomly divided into groups, and sensitised by an i.p. injection of ovalbumin (OVA, Sigma) on day zero and day fourteen. On the twentieth day, the mice were subjected to a challenge test by i.n. (intranasal) application of OVA (positive control or test groups) or PBS (negative control). 48 hours after i.n. application of OVA, the animals were anaesthetized and the lungs were rinsed with 1 mL of PBS. The cells were separated on Cytospin 3 cytocentrifuge (Shandon). The cells were stained in Diff-Quick (Dade) and the percentage of eosinophils was determined by differential counting of at least 100 cells.

Fluticasone (GlaxoWellcome) and beclomethasone (Pliva d.d.) were used as standard substances, with positive and negative control.

The compounds were administered daily i.n. or i.p. in different doses 2 days before the challenge test and up to the completion of the test.

Compounds 1 and 2 statistically significantly reduced (t-test, p<0.05) the number of eosinophils in the lung rinse with respect to positive control.

Cold Stress Model

Male Wistar rats with a body weight of 200-250 g (our own breeding) were randomly divided into groups. The carrier (lactose) in the volume of 0.5 mL/100 g s.c. was applied to the negative and positive control group. Test substances and the standard were applied once daily over three days in the dose of 2 mg/kg in the volume of 0.5 mL/100 g of body weight. The standard was applied in the dose of 1 mg/kg, in the volume of 0.5 mL/100 g of body weight.

On day three, 2 hours after the last treatment, all animals, except for the negative control group, were subjected to cold stress at 4° C. for 1 hour. After the stress, the animals were anaesthetized with thiopental (Pliva d.d.) and blood from all animals was drawn on K2 EDTA into test tubes. Plasma samples were frozen at −70° C. Corticosterone levels were determined by fluorimetric method according to Silber. Thymuses were removed from animals and weighed, and their weights were compared with the negative and positive control. Standards, fluticasone (GlaxoWellcome) and budesonide (Steraloids), statistically significantly reduced corticosterone plasma levels and reduced the weight of the thymus (P<0.05; T-test). Corticosterone levels and thymus weights for compound 1 were on the level of those of the control group of animals subjected to stress.

SYNTHETIC METHODS AND EXAMPLES

Precursors

In the following examples of methods of preparation, which in no way limit the uniqueness of the invention, the synthesis of the compound of Formula I from macrolide precursors M1-M5 and steroid precursors D1-D9 and nonsteroidal precursors D10, D11, D12, and D13 is described.

Macrolide Subunits

Macrolide subunits M1-M5 are compounds represented by the following general structure:

TABLE 1

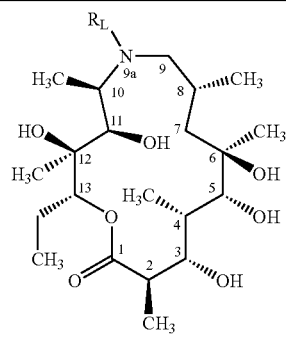

| | $R_L$ | Molecular formula | $MH^+$ |
|---|---|---|---|
| M1 | H | $C_{21}H_{41}NO_7$ | 420.2 |
| M2 | $CH_2CH_2CN$ | $C_{24}H_{44}N_2O_7$ | 473.3 |
| M3 | $CH_2CH_2C(O)OCH_3$ | $C_{25}H_{47}NO_9$ | 506.2 |
| M4 | $CH_2—(CH_2)_2—NH_2$ | $C_{24}H_{48}N_2O_7$ | 477.4 |
| M5 | $CH_2—(CH_2)_2—OH$ | $C_{24}H_{47}NO_8$ | 478.4 |

Method A a) Compound M1 (480 mg; 1.1 mmol) was dissolved in 10 mL of acrylonitrile and the reaction mixture was heated at 95° C. for 24 hours. Subsequently, the solvent was evaporated under reduced pressure. 500 mg of the compound M2 was obtained, which was used for further synthesis without previous purification.

b) Compound M2 (500 mg) was dissolved in 20 mL of absolute ethanol and hydrogenated with the catalyst $PtO_2$ (60 mg) for two days at the pressure of 40 atm. The mixture was purified was purified on a silica gel column, eluent $CHCl_3$:MeOH:$NH_4OH$=6:1:0.1. 193 mg of compound M4 was obtained. The properties of compounds M1, M2 and M4 are given in Table 1.

Method B a) Compound M1 (1 g; 2.4 mmol) was dissolved in 30 mL of methylacrylate. The reaction mixture was heated at the temperature of 90° C. overnight. The solvent was then evaporated under reduced pressure. 1.08 g of raw compound M3 was obtained.

b) Lithium aluminium hydride (225 mg) was added into 30 mL of dry THF and 1 g of compound M3 dissolved in 10 mL THF was added in a flow of argon. The reaction mixture was stirred at the temperature from 0 to 5° C. for 1 hour. Then water was added to the mixture to destroy the excess lithium aluminium hydride (until the colour changed to white). The reaction mixture was then filtered and the filtrate was evaporated under reduced pressure. 784 mg of product M5 was obtained. The mixture obtained was purified on a silica gel column, eluent CHCl$_3$:MeOH:NH$_4$OH=6:1:0.1.

The properties of compounds M3 and M5 are given in Table 1.

Steroid Subunits

Steroid subunits D1-D9 are compounds represented by the following general structure:

TABLE 2

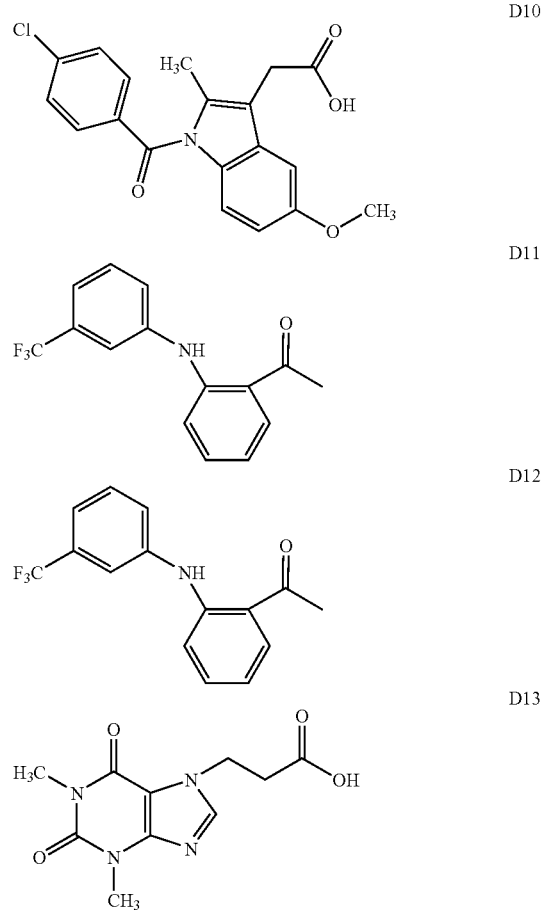

| C/1-C/2 bond | $R^a$ | $R^b$ | $R^d$ | $R^e$ | $R^f$ | Molecular formula |
|---|---|---|---|---|---|---|
| D1 | double | F | H | OH | CH$_3$ | OH | $C_{21}H_{27}FO_5$ |
| D2 | double | H | H | OCH$_3$ | H | OH | $C_{21}H_{28}O_5$ |
| D3 | double | F | H | OH | H | OH | $C_{20}H_{25}FO_5$ |
| D4 | single | H | H | OH | H | OH | $C_{20}H_{28}O_5$ |
| D5 | double | F | H | H | CH$_3$ | OH | $C_{21}H_{27}FO_4$ |
| D6 | double | Cl | H | OH | H | Cl | $C_{20}H_{24}Cl_2O_4$ |
| D7 | double | F | F | | DDO | OH | $C_{23}H_{28}F_2O_6$ |
| D8 | double | F | F | OH | CH$_3$ | OH | $C_{21}H_{26}F_2O_5$ |
| D9 | single | H | H | H | H | OH | $C_{20}H_{28}O_4$ |

DDO = 2,2-dimethyl-1,3-dioxazolone

Nonsteroidal Subunits

Precursors for the synthesis are nonsteroidal anti-inflammatory drugs (NSAID), such as aceclofenac, acemetacin, acetaminophen, acetaminosalol, acetyl-salicylic acid, acetyl-salicylic-2-amino-4-picoline-acid, 5-aminoacetylsalicylic acid, alclofenac, amino-profen, amfenac, anileridine, bendazac, benoxaprofen, bermoprofen, α-bisabolol, bromfenac, 5-bromosalicylic acid acetate, bromosaligenin, bucloxic acid, butibufen, carprofen, chromoglycate, cinmetacin, clindanac, clopirac, sodium diclofenac, diflunisal, ditazol, enfenamic acid, etodolac, etofenamate, felbinac, fenbufen, fenclozic acid, fendosal, fenoprofen, fentiazac, fepradinol, flufenamic acid, flunixin, flunoxaprofen, flurbiprofen, glutametacin, glycol salicylate, ibufenac, ibuprofen, ibuproxam, indomethacin, indoprofen, isofezolac, isoxepac, isoxicam, ketoprofen, ketorolac, lomoxicam, loxoprofen, meclofenamic acid, mefenamic acid, meloxicam, mesalamine, metiazinic acid, mofezolac, montelukast, naproxen, niflumic acid, olsalazine, oxaceprol, oxaprozin, oxyphenbutazone, parsalmide, perisoxal, phenyl-acethyl-salicylate, phenylbutazone, phenylsalicylate, pyrazolac, piroxicam, pirprofen, pranoprofen, protizinic acid, salacetamide, salicylamide-O-acetyl acid, salicylsulphuric acid, salicin, salicylamide, salsalate, sulindac, suprofen, suxibutazone, tenoxicam, tiaprofenic acid, tiaramide, tinoridine, tolfenamic acid, tolmetin, tropesin, xenbucin, ximoprofen, zaltoprofen, zomepirac, tomoxiprol, zafirlukast, and some example of precursors are indomethacin (D10), flufenamic acid (D11), flunixin (D12) and 2-methoxycarbonylethyltheophylline (D13):

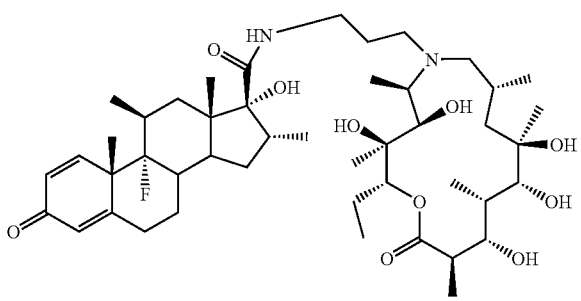

Example 1

Compound 1: (I; M=M4, D=D1)

Compound D1 (825 mg; 2.18 mmol) was dissolved in 15 mL of dry dichlormethane in a flow of argon. Subsequently, 2.86 mL of triethylamine, 601 mg of hydroxybenzotriazole, 1.82 g of macrolide M4 (2.18 mmol) and 3.1 g of 1-(3-dimethylaminopropyl)-3-ethylcarbodiimide hydrochloride were added into the solution. The reaction mixture was stirred at room temperature overnight. The solvent was evaporated under reduced pressure. The mixture obtained was purified on a silica gel column, eluent CHCl$_3$:MeOH:NH$_4$OH=6:1:0.1. 1.44 g of compound 1 was obtained; MS (m/z): 837.5 [MH]$^+$.

IR (KBr) cm$^{-1}$: 3422, 2938, 2874, 1710, 1663, 1624, 1560, 1528, 1458, 1376, 1302, 1245, 1176, 1139, 1089, 1052, 1036, 1012, 959, 929, 894, 816, 754, 706, 669.

Example 2

Compound 2: (I; M=M4, D=D5)

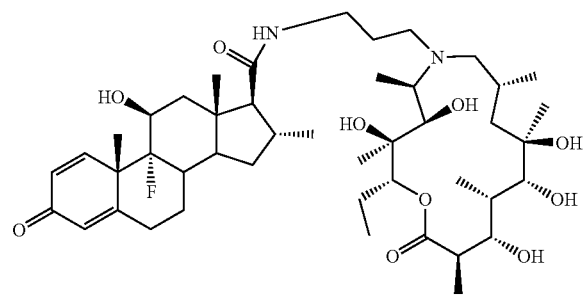

Compound D5 (57.8 mg; 0.16 mmol) was dissolved in 5 mL of dry dichlormethane in a flow of argon. 0.209 mL of triethylamine was added to the solution, clarifying it. Subsequently, 43.9 mg of hydroxybenzotriazole, macrolide M4 (76 mg; 0.1595 mmol) and 129.2 mg of 1-(3-dimethylaminopropyl)-3-ethylcarbodiimide hydrochloride were added. The reaction mixture was stirred at room temperature overnight. The solvent was evaporated under reduced pressure. The mixture obtained was purified on a silica gel column, eluent CHCl$_3$:MeOH:NH$_4$OH=6:1:0.1. 32 mg of compound 2 was obtained; MS (m/z): 821.4 [MH]$^+$. IR (KBr) cm$^{-1}$: 3423, 2939, 2876, 1718, 1664, 1625, 1560, 1541, 1458, 1376, 1353, 1296, 1249, 1178, 1089, 1054, 975, 959, 928, 889, 828, 811, 750, 669.

Example 3

Compound 3: (I; M=M4, D=D3)

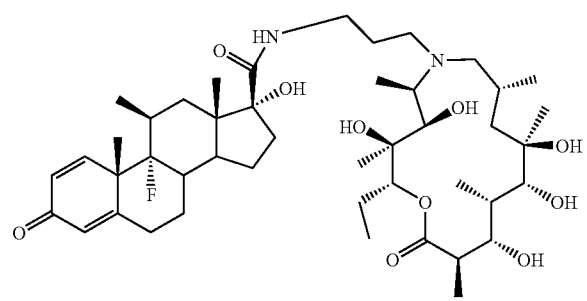

Compound D3 (165 mg; 0.453 mmol) was dissolved in 10 mL of dry dichlormetane. 0.595 mL of triethylamine was added to the solution. Subsequently, 125 mg of hydroxybenzotriazole, macrolide M4 (216 mg; 0.453 mmol) and 644 mg of 1-(3-dimethylaminopropyl)-3-ethylcarbodiimide hydrochloride were added to the reaction mixture. The reaction mixture was stirred at room temperature for 24 hours. The solvent was evaporated under reduced pressure. The mixture obtained was purified on a silica gel column, eluent CHCl$_3$:MeOH:NH$_4$OH=6:1:0.1. 241 mg of compound 3 was obtained; MS (m/z): 823.7 [MH]$^+$.

Example 4

Compound 4: (I; M=M4 D=D2)

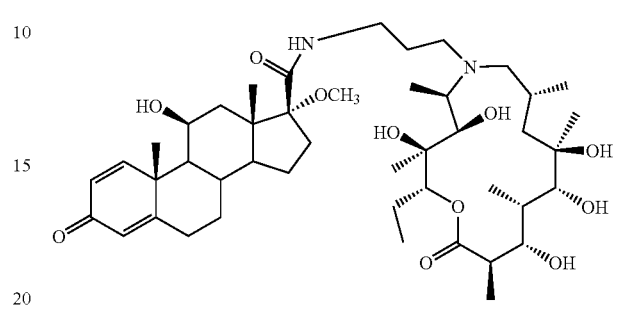

Compound D2 (337 mg; 0.936 mmol) was dissolved in 15 mL of dry dichlormethane. 1.228 mL of triethylamine, 258 mg of hydroxybenzotriazole, 445.7 mg of macrolide M4 (0.936 mmol) and 1.331 g 1-(3-dimethylaminopropyl)-3-ethylcarbodiimide hydrochloride were added to the solution. The reaction mixture was stirred at room temperature for 24 hours. The solvent was evaporated under reduced pressure. The product obtained was purified on a silica gel column, eluent CHCl$_3$:MeOH:NH$_4$OH=6:1:0.1. 490 mg of compound 4 was obtained; MS (m/z): 819.7 [MH]$^+$. IR (KBr) cm$^{-1}$: 3423, 2969, 2919, 2850, 2819, 2779, 1719, 1701, 1655, 1642, 1561, 1523, 1460, 1375, 1347, 1263, 1212, 1161, 1098, 1071, 1040, 959, 939, 888.

Example 5

Compound 5: (I; M=M4, D=D4)

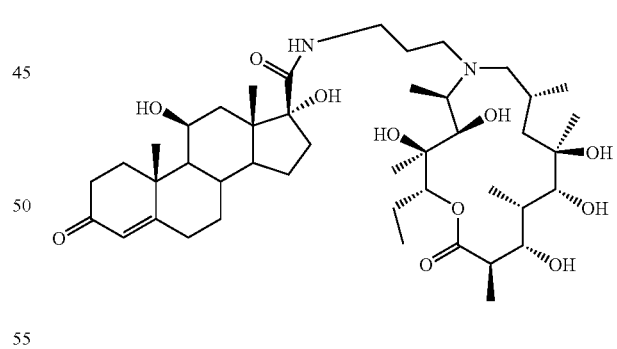

446 mg of D4 (1.28 mmol) acid was dissolved in 15 mL of dry dichloromethane in a flow of argon. 1.68 mL of triethylamine, 353.2 mg of hydroxybenzotriazole, 610.2 mg of macrolide M4 (1.281 mmol) and 1.822 g of 1-(3-dimethylaminopropyl)-3-ethylcarbodiimide hydrochloride were added to the solution. The reaction mixture was stirred at room temperature for 24 hours. The solvent was evaporated under reduced pressure. The mixture obtained was purified on a silica gel column, eluent CHCl$_3$:MeOH:NH$_4$OH=6:1:0.1. 516 mg of compound 5 was obtained; MS (m/z): 807.5 [MH]$^+$. IR (KBr) cm$^{-1}$: 3414, 2936, 2874, 2129, 1703, 1655, 1560, 1541, 1535, 1458, 1357, 1322, 1238, 1186, 1162, 1120, 1092, 1049, 998, 964, 936, 897, 871, 753, 703.

Example 6

Compound 6: (I; M=M4, D=D7)

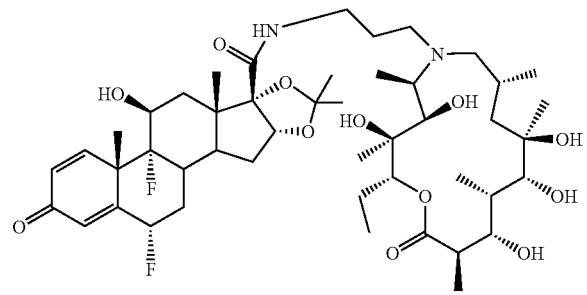

Compound D7 (570 mg; 0.57 mmol) was dissolved in 20 mL of dimethylformamide. 0.755 mL of diisopropylethylamine and 154 mg (2 eq) of 1-hydroxybenzotriazole were added. Subsequently, compound M4 (271 mg; 0.57 mmol) and 1-(3-dimethylaminopropyl)-3-ethylcarbodiimide hydrochloride (391 mg, 4 eq) were added. The reaction mixture was stirred for 24 hours at 100° C. under reflux in an inert atmosphere. The solvent was then evaporated, and the compound was purified on a silica gel column in the solvent system $CHCl_3$: $MeOH:NH_4OH$=6:1:0.1. 220 mg of compound 6 was isolated; MS (m/z): 897.5 [MH]+.

Example 7

Compound 7: (I; M=M4, D=D10)

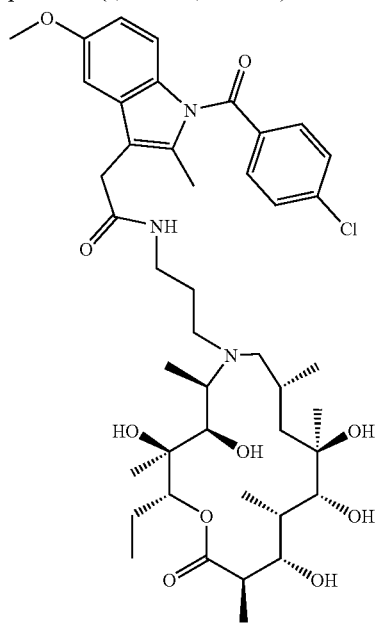

Indomethacin D10 (165.2 mg; 0.4618 mmol) was dissolved in 20 mL of dichlormethane. 0.501 mL (3.602 mmol) of triethylamine and 124.8 mg (0.9236 mmol) of 1-hydroxybenzotriazole were added. Subsequently, compound M4 (220 mg; 0.4618 mmol) and 1-(3-dimethylaminopropyl)-3-ethylcarbodiimide hydrochloride (317 mg, 1.8472 mmol) were added. The reaction mixture was stirred for 24 hours at room temperature in an inert atmosphere. The solvent was then evaporated, and the compound was purified on a silica gel column in the solvent system $CHCl_3$: $MeOH:NH_4OH$=6:1:0.1. 190 mg of compound 7 was isolated; MS (m/z): 816.4 [MH]+. IR (KBr) $cm^{-1}$: 3422, 2972, 2935, 2876, 1655, 1560, 1542, 1535, 1478, 1458, 1400, 1372, 1352, 1323, 1290, 1260, 1226, 1179, 1150, 1090, 1053, 1037, 1015, 958, 926, 911, 833, 804, 755, 664

Example 8

Compound 8: (I; M=M5 D=D5)

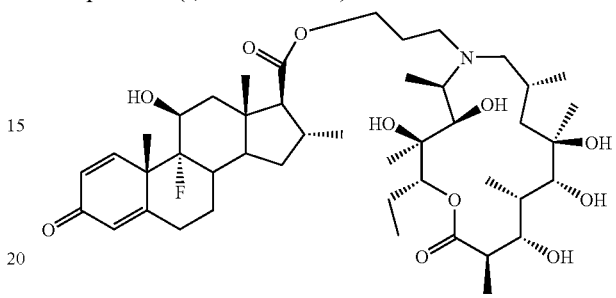

Compound D5 (32.6 mg; 0.09 mmol) was dissolved in 5 mL of dry DMF in a flow of argon. The solution was cooled to −10° C. and then 1,1-carbonyldiimidazole (30 mg; 0.18 mmol) dissolved in 3 mL of dry DMF was added. The reaction mixture was stirred overnight at the temperature of −5° C. Subsequently, compound M5 (43 mg; 0.09 mmol) dissolved in 3 mL of dry DMF was added. The reaction mixture was heated at 100° C. for two days. DMF was evaporated under reduced pressure, and the residue was purified on a silica gel column, eluent $CHCl_3:MeOH:NH_4OH$=6:1:0.1. 22 mg of compound 8 was obtained; MS (m/z): 822.6[MH]+.

Example 9

Compound 9: (I; M=M5, D=D10)

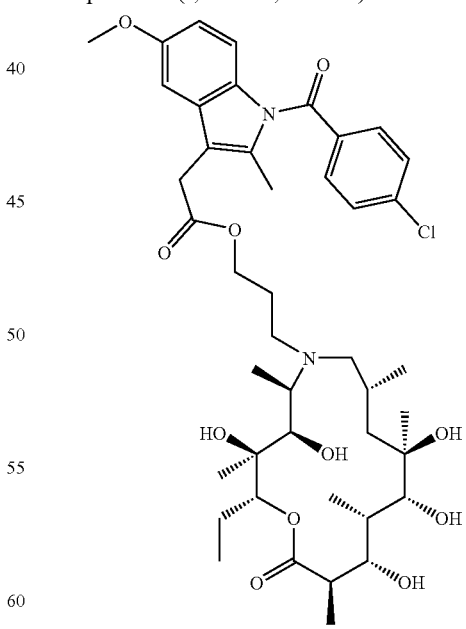

Indomethacin D10 (32.1 mg; 0.09 mmol) was dissolved in dry DMF (5 mL), in a flow of argon. The solution was cooled to −10° C. and then 1,1-carbonyldiimidazole (30 mg; 0.18 mmol) dissolved in 3 mL of dry DMF was added. The reaction mixture was stirred overnight at the temperature of −5° C.

Subsequently, compound M5 (43 mg; 0.09 mmol) dissolved in 3 mL of dry DMF was added. The reaction mixture was heated at 100° C. for two days. DMF was evaporated under reduced pressure, and the residue was purified on a silica gel column, eluent CHCl$_3$:MeOH:NH$_4$OH=6:1:0.1. 25 mg of compound 9 was obtained; MS (m/z): 817.7[MH]$^+$.

Example 10

Compound 10: (I; M=M4, D=D6)

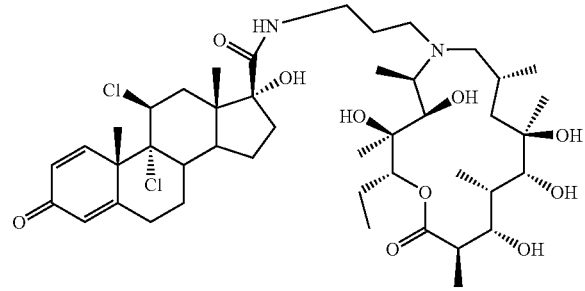

115 mg of D6 acid (0.29 mmol) was dissolved in 15 mL of dry dichloromethane, under flow of argon. 0.38 mL of triethylamine, 80 mg of hydroxybenzotriazole, 138 mg of macrolide M4 (0.29 mmol) and 235 mg of 1-(3-dimethylaminopropyl)-3-ethylcarbodiimide hydrochloride were added to the solution. The reaction mixture was stirred at room temperature for 24 hours. The solvent was evaporated under reduced pressure, and the residue was purified on a silica gel column, eluent CHCl$_3$:MeOH:NH$_4$OH=6:1:0.1. 70 mg of compound 10 was obtained; MS (m/z): 857.8 [MH]$^+$.

Example 11

Compound 11: (I; M=M4 D=D8)

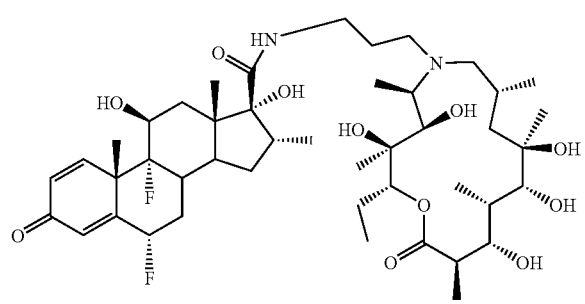

Compound D8 (100 mg; 0.25 mmol) was dissolved in 5 mL of dry dichlormethane in a flow of argon. Subsequently, 0.12 mL of triethylamine, 69.6 mg of hydroxybenzotriazole, 120.1 mg of macrolide M4 (0.25 mmol) and 204.5 mg of 1-(3-dimethylaminopropyl)-3-ethylcarbodiimide hydrochloride were added into the solution. The reaction mixture was stirred at room temperature overnight. The solvent was evaporated under reduced pressure. The mixture obtained was purified on a silica gel column, eluent CHCl$_3$:MeOH:NH$_4$OH=6:1:0.1. 70 mg of compound 11 was obtained; MS (m/z): 855.4 [MH]$^+$. IR (KBr) cm$^{-1}$: 3422, 2963, 2930, 2875, 2855, 1734, 1718, 1693, 1665, 1624, 1544, 1459, 1376, 1262, 1205, 1167, 1093, 1049, 1030, 958, 901, 864, 802, 737, 702.

Example 12

Compound 12: (I; M=M4, D=D9)

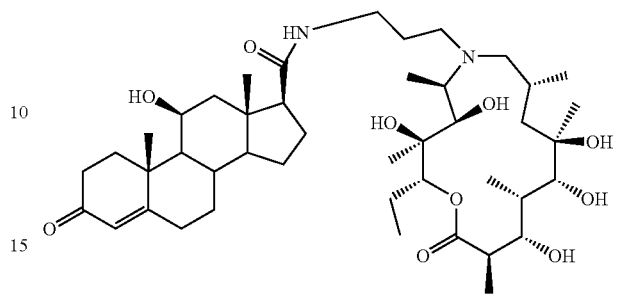

Compound D9 (100 mg; 0.30 mmol) was dissolved in 5 mL of dry dichlormethane in a flow of argon. Subsequently, 0.394 mL of triethylamine, 83 mg of hydroxybenzotriazole, 143.3 mg of macrolide M4 (0.30 mmol) and 244 mg of 1-(3-dimethylaminopropyl)-3-ethylcarbodiimide hydrochloride were added into the solution. The reaction mixture was stirred at room temperature overnight. The solvent was evaporated under reduced pressure. The mixture obtained was purified on a silica gel column, eluent CHCl$_3$:MeOH:NH$_4$OH=6:1:0.1. 107.5 mg of compound 12 was obtained; MS (m/z): 791.6 [MH]$^+$. IR (KBr) cm$^{-1}$: 3440, 3367, 2967, 2938, 2877, 1706, 1668, 1656, 1619, 1545, 1532, 1510, 1459, 1379, 1367, 1351, 1273, 1257, 1239, 1185, 1163, 1087, 1057, 1033, 973, 957, 930, 897, 869, 812, 736, 704.

Example 13

Compound 13: (I; M=M4, D=D11)

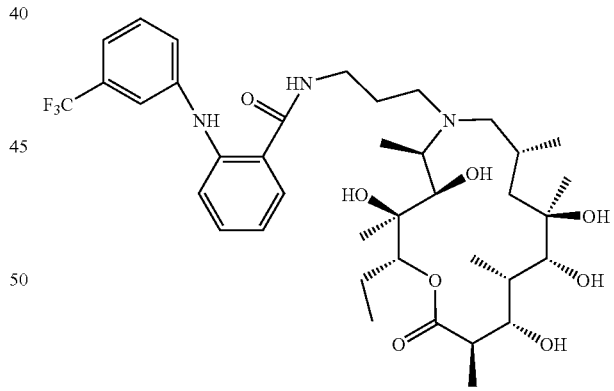

Compound D11 (82 mg; 0.29 mmol) was dissolved in 5 mL of dry dichlormethane in a flow of argon. Subsequently, 0.380 mL of triethylamine, 80 mg of hydroxybenzotriazole, 138 mg of macrolide M4 (0.29 mmol) and 235 mg of 1-(3-dimethylaminopropyl)-3-ethylcarbodiimide hydrochloride were added into the solution. The reaction mixture was stirred at room temperature overnight. The solvent was evaporated under reduced pressure. The mixture obtained was purified on a silica gel column, eluent CHCl$_3$:MeOH:NH$_4$OH=90:9:1.5. 112 mg of compound 13 was obtained; MS (m/z): 740.4 [MH]$^+$.

Example 14

Compound 14: (I; M=M4, D=D12)

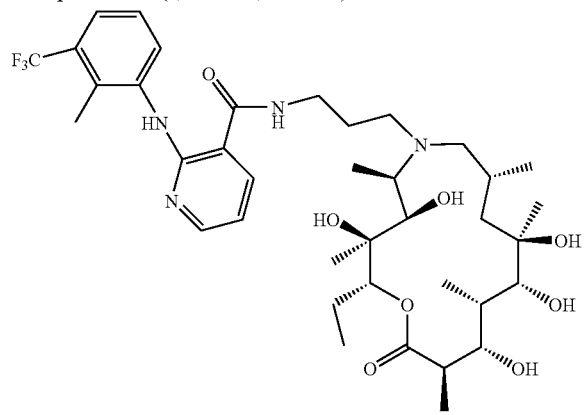

Compound D12 (86 mg; 0.29 mmol) was dissolved in 5 mL of dry dichlormethane in a flow of argon. Subsequently, 0.38 mL of triethylamine, 80 mg of hydroxybenzotriazole, 138 mg of macrolide M4 (0.29 mmol) and 235 mg of 1-(3-dimethylaminopropyl)-3-ethylcarbodiimide hydrochloride were added into the solution. The reaction mixture was stirred at room temperature overnight. The solvent was evaporated under reduced pressure. The mixture obtained was purified on a silica gel column, eluent $CHCl_3$:MeOH:$NH_4OH$=90:9:1.5. 100 mg of compound 14 was obtained; MS (m/z): 755.4 $[MH]^+$.

Example 15

Compound 15: (I; M=M4, D=D13)

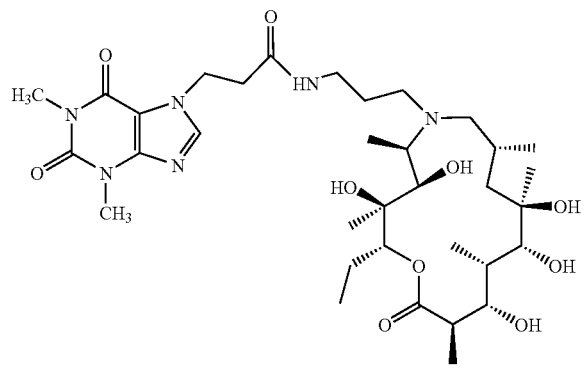

D13a D13 Methyl Ester

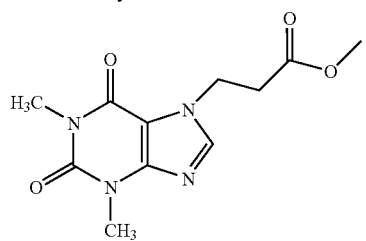

A solution of theophylline (1,80 g, 10 mmol), methyl acrylate (30 mL), and tBuOH (0.96 mL, 10 mmol) in THF (200 mL) was treated with KOtBu (56.1 mg, 0.5 mmol), heated at 130° C. for 24 h, cooled, diluted with $CH_2Cl_2$ and washed with $H_2O$. The organic layer was dried over $Na_2SO_4$, evaporated and purified on a silica gel column in the solvent system $CH_2Cl_2$:MeOH:$NH_4OH$=6:1:0.1. 1.4 g of the compound D13a was obtained. MS (m/z): 267.3 $[MH]^+$ 2-methoxycarbonylethyltheophylline (D13)

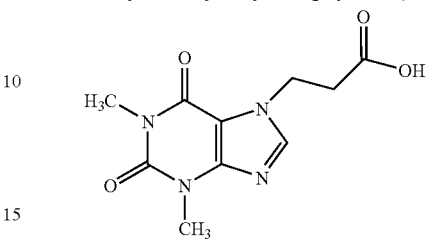

A solution of D13a (717 mg, 2.70 mmol) in THF was treated with solution of LiOH (226.6 mg, 5.40 mmol) in water (5 mL) and stirred vigorously for 5 min. HCl (1.0 N, 8 mL) was added, followed by additional water (10 mL). The THF was removed under vacuum and the resulting solid was isolated by filtration to give 450 mg of D13. MS (m/z): 253.3 $[MH]^+$ A solution of D13 (187 mg; 0.744 mmole) in 10 mL of dichloromethane was treated with 0.828 mL of triethylamine and 201 mg of 1-hydroxybenzotriazole. Compound M4 (354.4 mg; 0.744 mmole) and 1-(3-dimethylaminopropyl)-3-ethyl-carbodiimide hydrochloride (511 mg) were added. The reaction mixture was stirred at room temperature for 24 h. The solvent was then evaporated and the compound purified on a silica gel column in the solvent system $CHCl_3$: MeOH:$NH_4OH$=6:1:0.1. 200 mg of compound D15 was isolated. MS (m/z): 711,9 $[MH]^+$. IR($cm^{-1}$)/KBr: 3450, 3111, 2974, 2877, 1706, 1659, 1604, 1550, 1475, 1459, 1409, 1376, 1353, 1240, 1225, 1184, 1164, 1140, 1089, 1053, 1035, 976, 958, 929, 898, 850, 810, 751, 706, 666, 621.

Example 16

Compound 18

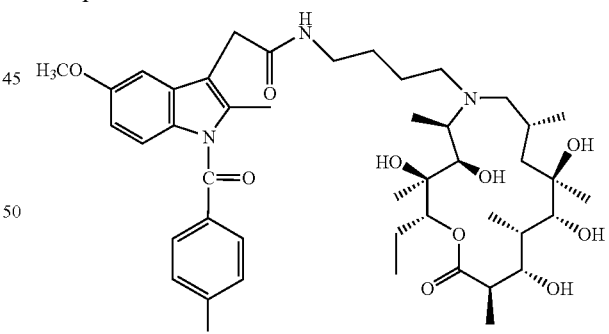

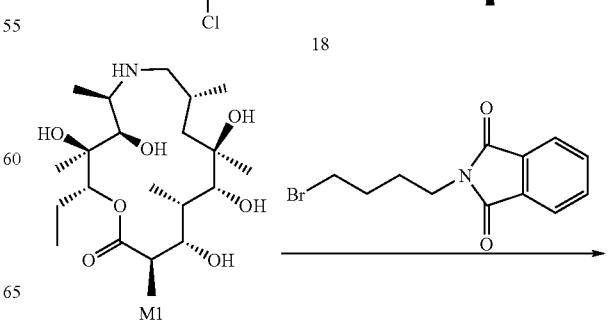

-continued

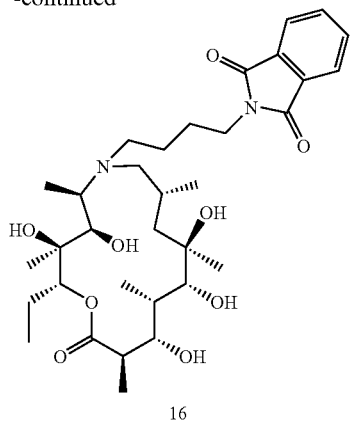

16

In a solution of compound M1 (1 g, 2.384 mmol) and N,N-diisopropylethylamine (4.054 ml, 23.84 mmol) in 60 ml acetonitrile N-(4-bromobutyl)-phthalimide (6.726 g; 23.84 mmol) was added. The reaction mixture was stirred at 80° C. for. 38 hours. After evaporation of the solvent, mixture was diluted with EtOAc and water. The organic layer was separated and dried over $Na_2SO_4$. The solvent was evaporated under reduced pressure and the obtained mixture was purified on a silica gel column, eluent $CH_2Cl_2$:MeOH:$NH_4$OH=90:8:1. 580 mg of the compound 16 was obtained. MS (m/z): 621,80 [MH]$^+$. IR(cm$^{-1}$)/KBr: 3483, 3061, 2973, 2937, 2876, 1773, 1713, 1612, 1467, 1439, 1398, 1372, 1356, 1267, 1174, 1137, 1089, 1053, 999, 958, 933, 902, 863, 809, 721, 623.

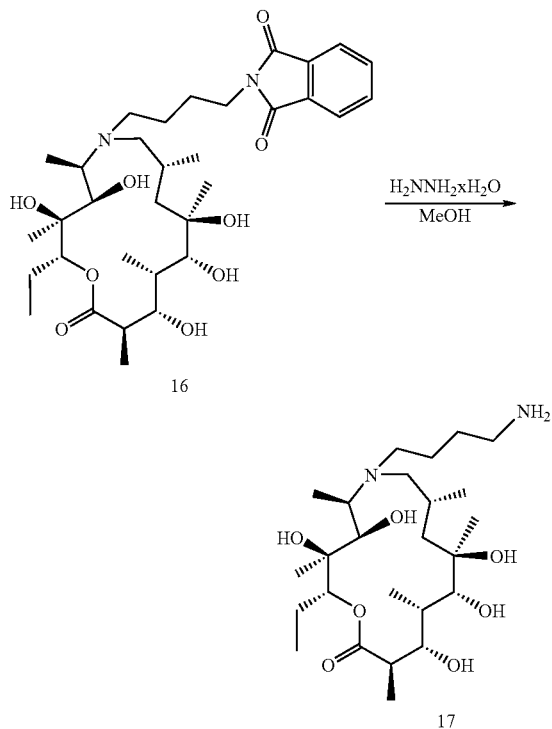

In a solution of compound 16 (250 mg, 0.403 mmol) in 25 ml methanol hydrazine hydrate (0.043 ml, 0.886 mmol) was added. Reaction mixture was stirred at 65° C. for 3 hours. After evaporation of the solvent, mixture was diluted with EtOAc and water. The organic layer was dried over $Na_2SO_4$. The solvent was evaporated under reduced pressure and obtained mixture was purified on a silica gel column, eluent $CH_2Cl_2$:MeOH:$NH_4$OH 6:1:0.1. 151 mg of the compound 17 was obtained. MS (m/z): 491,66 [MH]$^+$. IR(cm$^{-1}$)/KBr: 3415, 2974, 2937, 2876, 1720, 1599, 1459, 1376, 1352, 1308, 1268, 1176, 1139, 1090, 1055, 1038, 958, 900, 850, 810, 737, 705, 671.

Indomethacin D10 (73 mg; 0.204 mmole) was dissolved in 10 mL of dry dichloromethane. Triethylamine (0.222 mL) and 55 mg of 1-hydroxybenzotriazole were added and then the compound 17 (100 mg; 0.204 mmole) and 1-(3-dimethylaminopropyl)-3-ethyl-carbodiimide hydrochloride (156 mg). The reaction mixture was stirred in an inert atmosphere at room temperature for 24 h. The solvent was then evaporated under reduced pressure and the compound was purified on a silica gel column, eluent $CH_2Cl_2$:MeOH:$NH_4$OH=90:9:1.5. 140 mg of compound 18 was obtained; MS (m/z): 830.91 [MH]$^+$. IR(cm$^{-1}$)/KBr: 3417, 3087, 2972, 2935, 2876, 1709, 1681, 1658, 1596, 1529, 1478, 1457, 1400, 1372, 1357, 1322, 1289, 1261, 1226, 1179, 1150, 1090, 1054, 1037, 1015, 958, 926, 912, 833, 805, 755, 736, 702, 664.

Example 17

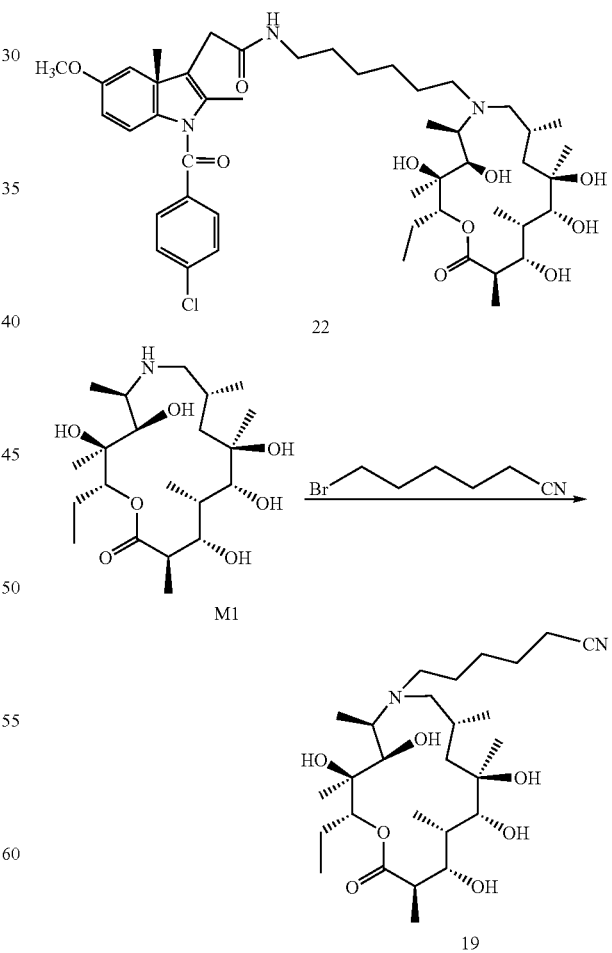

In a solution of compound M1 (2 g; 4,767 mmol) and N,N-diisopropylethylamine (8,10 ml; 47,67 mmol) in acetonitrile (80 ml) 6-bromohexanenitrile (6.32 ml; 47,67 mmol) was added. Reaction mixture was stirred at 80° C. for 21 hours. After evaporation of the solvent, mixture was diluted with dichlormethane and water. The organic layer was dried over $Na_2SO_4$. The solvent was then evaporated under reduced pressure and the compound was purified on a silica gel column, eluent $CH_2Cl_2$:MeOH:$NH_4OH$=90:9:1.5. 532 mg of the compound 19 was obtained. MS (m/z): 515.70 [MH]$^+$. IR(cm$^{-1}$)/KBr: 3444, 2973, 2937, 2875, 2247 (C≡N), 1712, 1637, 1459, 1375, 1352, 1307, 1265, 1179, 1139, 1090, 1052, 1004, 958, 901, 860, 810, 773, 750, 705, 670.

0.174 mmole) and 1-(3-dimethylaminopropyl)-3-ethyl-carbodiimide hydrochloride (133 mg) were added. The reaction mixture was stirred in an inert atmosphere at room temperature for 24 h. The solvent was then evaporated under reduced pressure and the compound was purified on a silica gel column in the solvent system $CH_2Cl_2$:MeOH:$NH_4OH$=90:8:1. 105 mg of compound 22 was obtained; MS (m/z): 858.81 [MH]$^+$.

Example 18

Compound 23

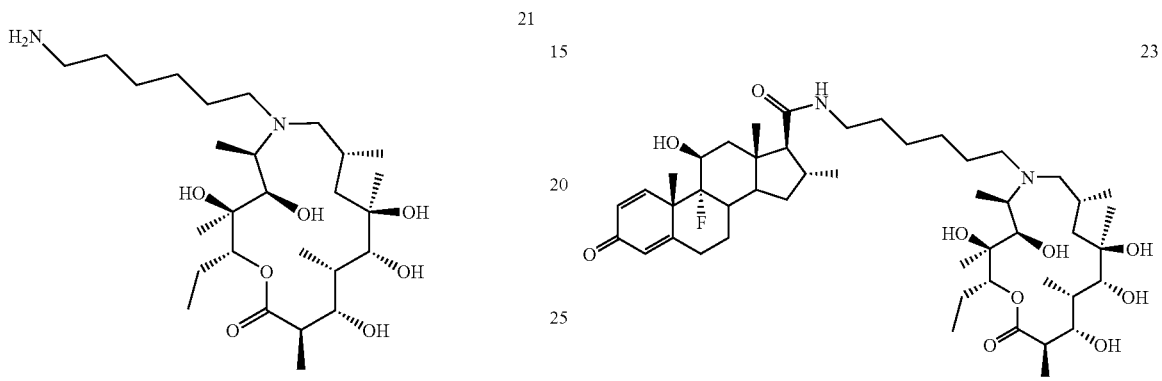

The macrolide 19 (532 mg; 1.034 mmole) was dissolved in 25 mL of absolute ethanol and hydrogenated in a reactor with the catalyst $PtO_2$ (53 mg) under pressure of 40 atm of $H_2$ for 24 hours. The reaction mixture was filtered and the solvent was evaporated under reduced pressure. 463 mg of the mixture was obtained. The mixture was purified on a silica gel column, eluent $CH_2Cl_2$:MeOH:$NH_4OH$=6:1:0.1; 180 mg of amine 21 was obtained. MS (m/z): 519.74 [MH]$^+$.

Indomethacin D10 (62 mg; 0.174 mmole) was dissolved in 10 mL of dry dichloromethane. Triethylamine (0.189 mL), 47 mg of 1-hydroxybenzotriazole, the compound 21 (90 mg;

Desoxymethasone acid D5 (63 mg; 0.174 mmole) was dissolved in 10 mL of dry dichloromethane. Triethylamine (0.189 mL), 47 mg of 1-hydroxybenzotriazole, compound 21 (90 mg; 0.174 mmole) and 1-(3-dimethylaminopropyl)-3-ethyl-carbodiimide hydrochloride (133 mg) were added. The reaction mixture was stirred in an inert atmosphere at room temperature for 24 h. The solvent was then evaporated under reduced pressure and the compound was purified on a silica gel column in the solvent system $CH_2Cl_2$:MeOH: $NH_4OH$=90:8:1. 98 mg of compound 23 was obtained; MS (m/z): 863,77 [MH].

The invention claimed is:
1. A compound according to Formula I:

I wherein
M represents the macrolide subunit of the substructure II:

II wherein
R$^1$, R$^2$, R$^3$, R$^4$ and R$^5$ are, chosen independently of each other, from the group consisting of hydrogen, C$_1$-C$_4$ alkyl, C$_1$-C$_{10}$ alkanoyl, C$_1$-C$_{10}$ alkoxycarbonyl, C$_6$-C$_{14}$ arylmethoxycarbonyl, C$_6$-C$_{14}$ aroyl, C$_6$-C$_{14}$ arylalkyl, C$_1$-C$_{10}$ alkylsilyl and C$_1$-C$_{10}$ alkylsilylalkoxyalkyl;
R$_N$ represents the covalent link with X$^1$ of the chain L;
L represents the chain of the substructure III:

—X$^1$—(CH$_2$)$_m$-Q-(CH$_2$)$_n$—X$^2$— III wherein
X$^1$ is —CH$_2$— or —C(O)—;
X$^2$ is —NH— or —O—;
Q is —NH— or —CH$_2$—;
symbols m and n, independently, are whole numbers from 0 to 4;
with the proviso that if Q=NH, n cannot be 0;
wherein D is a steroid of the substructure IV:

IV wherein
R$^a$ and R$^b$ are chosen independently of each other from the group consisting of hydrogen and halogen;
R$^f$ is chosen from the group consisting of hydrogen, hydroxyl group, halogen or R$^f$ forms a carbonyl group with the carbon atom to which it is linked;
R$^c$ is a covalent link with X$^2$ of the chain L;
R$^d$ and R$^e$ are chosen independently from the group consisting of hydrogen, hydroxy, methyl, C$_1$-C$_4$ alkoxy or R$^d$ and R$^e$ together with the pertaining C-atoms to which they are attached represent 1,3-dioxolane ring which can be additionally mono or di-substituted with C$_1$-C$_{10}$ alkyl or C$_2$-C$_{10}$ alkenyl; and R$^j$ is chosen from the group consisting of hydrogen and chlorine;
or a pharmaceutically acceptable salt thereof.

2. A compound according to claim 1 wherein R$^1$, R$^2$, R$^3$, R$^4$ and R$^5$ are each independently chosen from the group consisting of hydrogen and C$_1$-C$_4$ alkyl.

3. The compound according to claim 1 wherein R$^1$, R$^2$, R$^3$, R$^4$ and R$^5$ are chosen independently from the group consisting of hydrogen and methyl.

4. The compound according to claim 1 wherein X$^1$ is CH$_2$ and X$^2$ is NH.

5. The compound according to claim 4 wherein m=1, n=1 and Q represents CH$_2$.

6. A compound according to claim 1 wherein substructure IV is chosen from the group consisting of

7. A compound according to claim 6 wherein substructure IV is

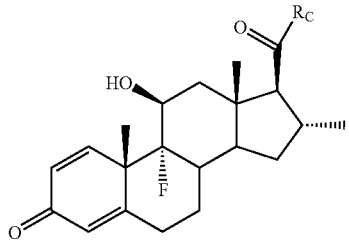

or a pharmaceutically acceptable salt thereof.

8. A compound according to claim 1 having the structure

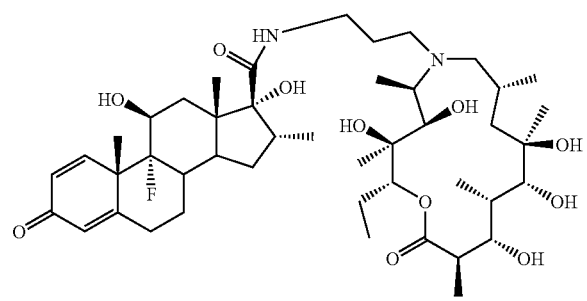

or a pharmaceutically acceptable salt thereof.

9. A compound according to claim 1 having the structure

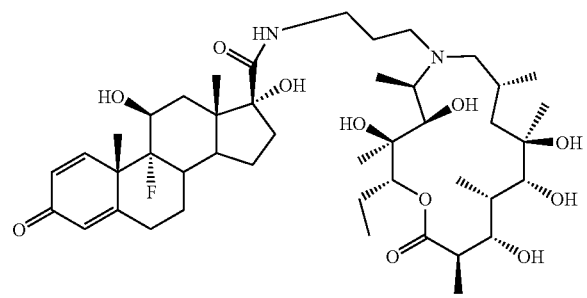

or a pharmaceutically acceptable salt thereof.

10. A compound according to claim 1 having the structure

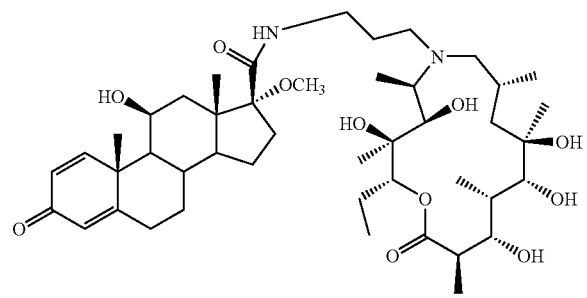

or a pharmaceutically acceptable salt thereof.

11. A compound according to claim 1 having the structure

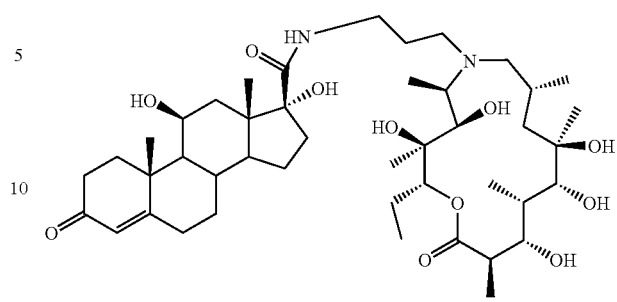

or a pharmaceutically acceptable salt thereof.

12. A compound according to claim 1 having the structure

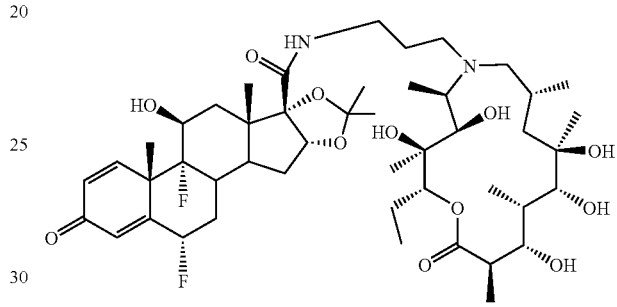

or a pharmaceutically acceptable salt thereof.

13. A compound according to claim 1 having the structure

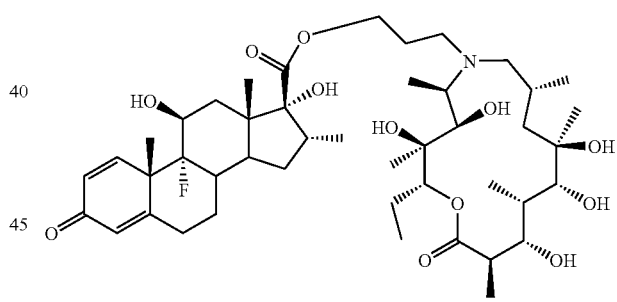

or a pharmaceutically acceptable salt thereof.

14. A compound according to claim 1 having the structure

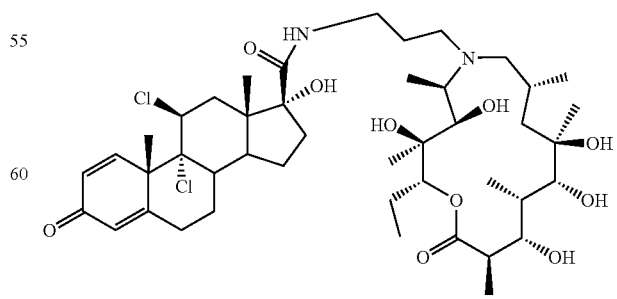

or a pharmaceutically acceptable salt thereof.

15. A compound according to claim 1 having the structure

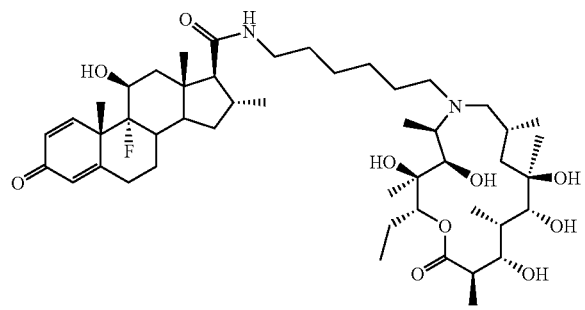

or a pharmaceutically acceptable salt thereof.

16. A compound according to claim 1 having the structure

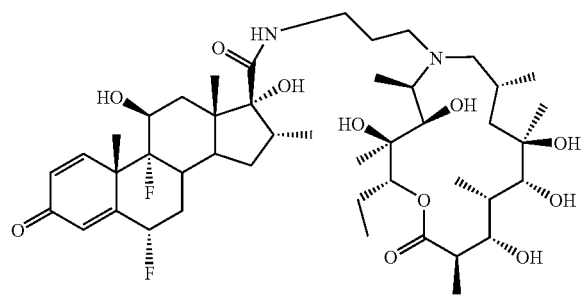

or a pharmaceutically acceptable salt thereof.

17. A compound according to claim 1 having the structure

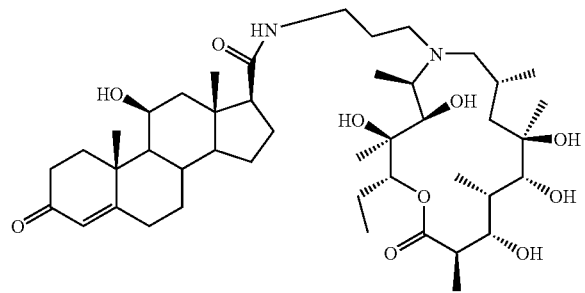

or a pharmaceutically acceptable salt thereof.

18. A compound having the structure

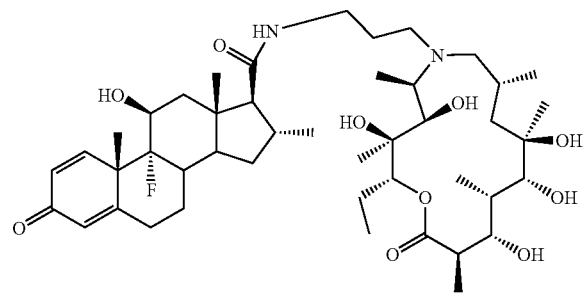

or a pharmaceutically acceptable salt thereof.

19. A compound having the structure

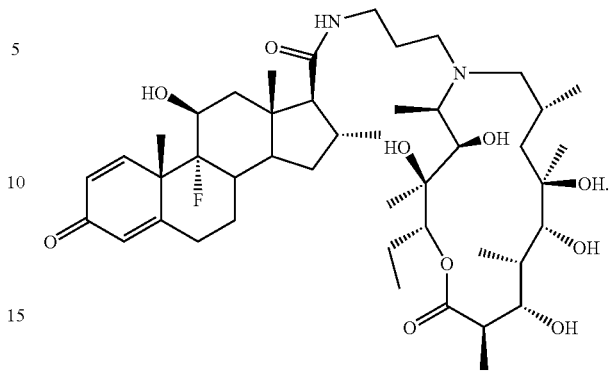

or a pharmaceutically acceptable salt thereof.

20. A pharmaceutical composition comprising a compound according to claim 1 or a pharmaceutically acceptable salt thereof together with a pharmaceutically acceptable diluent or carrier.

21. A pharmaceutical composition comprising a compound according to claim 18, or a pharmaceutically acceptable salt thereof, together with a pharmaceutically acceptable diluent or carrier.

22. A pharmaceutical composition comprising a compound according to claim 19 together with a pharmaceutically acceptable diluent or carrier.

23. A method of relieving an inflammatory disease, disorder, or condition or immune disorder selected from the group consisting of asthma, adult respiratory distress syndrome, chronic obstructive pulmonary disease, inflammatory bowel conditions, Crohn's disease, bronchitis, and cystic fibrosis comprising administering to a subject in need thereof a therapeutically effective amount of a compound according to claim 1 or a pharmaceutically acceptable salt thereof.

24. A method of relieving psoriasis, comprising administering to a subject in need thereof a therapeutically effective amount of a compound according to claim 1 or a pharmaceutically acceptable salt thereof.

25. A method of relieving chronic obstructive pulmonary disease, comprising administering to a subject in need thereof a therapeutically effective amount of a compound according to claim 10 or a pharmaceutically acceptable salt thereof.

26. A method of relieving asthma, comprising administering to a subject in need thereof a therapeutically effective amount of a compound according to claim 18 or a pharmaceutically acceptable salt thereof.

27. A method of relieving inflammatory bowel disease, comprising administering to a subject in need thereof a therapeutically effective amount of a compound according to claim 18 or a pharmaceutically acceptable salt thereof.

28. A method of relieving psoriasis, comprising administering to a subject in need thereof a therapeutically effective amount of a compound according to claim 18 or a pharmaceutically acceptable salt thereof.

29. A method according to claim 23, wherein the subject is a human.

30. A method according to claim 24, wherein the subject is a human.

31. A method according to claim 25, wherein the subject is a human.

32. A method according to claim 26, wherein the subject is a human.

33. A method according to claim 27, wherein the subject is a human.

34. A method according to claim 28, wherein the subject is a human.

35. A method of relieving chronic obstructive pulmonary disease, comprising administering to a subject in need thereof a therapeutically effective amount of a compound according to claim 1 or a pharmaceutically acceptable salt thereof.

36. A method according to claim 35, wherein the subject is a human.

37. A method of relieving asthma, comprising administering to a subject in need thereof a therapeutically effective amount of a compound according to claim 1 or a pharmaceutically acceptable salt thereof.

38. A method according to claim 37, wherein the subject is a human.

39. A method of relieving inflammatory bowel disease, comprising administering to a subject in need thereof a therapeutically effective amount of a compound according to claim 1 or a pharmaceutically acceptable salt thereof.

40. A method according to claim 39, wherein the subject is a human.

41. A method of relieving chronic obstructive pulmonary disease, comprising administering to a subject in need thereof a therapeutically effective amount of a compound according to claim 19.

42. A method according to claim 41, wherein the subject is a human.

43. A method of relieving asthma, comprising administering to a subject in need thereof a therapeutically effective amount of a compound according to claim 19.

44. A method according to claim 43, wherein the subject is a human.

45. A method of relieving inflammatory bowel disease, comprising administering to a subject in need thereof a therapeutically effective amount of a compound according to claim 19.

46. A method according to claim 45, wherein the subject is a human.

47. A method of relieving psoriasis, comprising administering to a subject in need thereof a therapeutically effective amount of a compound according to claim 19.

48. A method according to claim 47, wherein the subject is a human.

* * * * *

UNITED STATES PATENT AND TRADEMARK OFFICE
CERTIFICATE OF CORRECTION

| | | |
|---|---|---|
| PATENT NO. | : 7,579,334 B2 | Page 1 of 1 |
| APPLICATION NO. | : 10/830858 | |
| DATED | : August 25, 2009 | |
| INVENTOR(S) | : Mladen Mercep et al. | |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 781 days.

should read (*) Notice: Subject to any disclaimer, the term of this patent is extended or adjusted under 35 U.S.C. 154(b) by 1,067 days.

Signed and Sealed this

Twentieth Day of April, 2010

David J. Kappos
*Director of the United States Patent and Trademark Office*